(12) United States Patent
Suda et al.

(10) Patent No.: US 9,214,637 B2
(45) Date of Patent: Dec. 15, 2015

(54) CHALCOGEN-CONTAINING AROMATIC COMPOUND, ORGANIC SEMICONDUCTOR MATERIAL, AND ORGANIC ELECTRONIC DEVICE

(75) Inventors: Mitsuru Suda, Kitakyushu (JP); Takahiro Kai, Kitakyushu (JP); Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 336 days.

(21) Appl. No.: 13/877,112

(22) PCT Filed: Oct. 3, 2011

(86) PCT No.: PCT/JP2011/072782
§ 371 (c)(1),
(2), (4) Date: Mar. 29, 2013

(87) PCT Pub. No.: WO2012/050001
PCT Pub. Date: Apr. 19, 2012

(65) Prior Publication Data
US 2013/0207047 A1     Aug. 15, 2013

(30) Foreign Application Priority Data

Oct. 12, 2010  (JP) .................................. 2010-229961
Dec. 6, 2010   (JP) .................................. 2010-271875

(51) Int. Cl.
*H01L 51/00* (2006.01)
*C07D 493/04* (2006.01)
(Continued)

(52) U.S. Cl.
CPC .......... *H01L 51/0074* (2013.01); *C07D 493/04* (2013.01); *C07D 495/04* (2013.01);
(Continued)

(58) Field of Classification Search
None
See application file for complete search history.

(56) References Cited

U.S. PATENT DOCUMENTS 3,433,874 A * 3/1969 Geering ......................... 514/443

FOREIGN PATENT DOCUMENTS

| JP | 2009-246139 A | 10/2009 |
|----|---------------|---------|
| JP | 2009-246140 A | 10/2009 |
| JP | 2009-283786 A | 12/2009 |
| JP | 2009-302328 A | 12/2009 |
| JP | 2010-40829 A  | 2/2010  |

OTHER PUBLICATIONS

International Search Report for the Application No. PCT/JP2011/072782 mailed Dec. 13, 2011.
International Preliminary Report on Patentability for Application No. PCT/JP2011/072782 mailed Apr. 18, 2013.
(Continued)

*Primary Examiner* — J. L. Yang
(74) *Attorney, Agent, or Firm* — Cheng Law Group, PLLC

(57) ABSTRACT

Provided are a novel chalcogen-containing aromatic compound and an organic electronic device using the compound. This compound is a chalcogen-containing aromatic compound represented by the formula (1). Among the organic electronic devices each using this chalcogen-containing aromatic compound are an organic EL device, an organic TFT device, a photovoltaic device, and the like. In the formula (1): X represents oxygen, sulfur, or selenium; A represents an alkyl group, a cycloalkyl group, an alkenyl group, an alkynyl group, an aromatic hydrocarbon group, an aromatic heterocyclic group, or an amino group; and n's each independently represent an integer of 0 to 2, provided that a sum of two n's is 1 to 4.

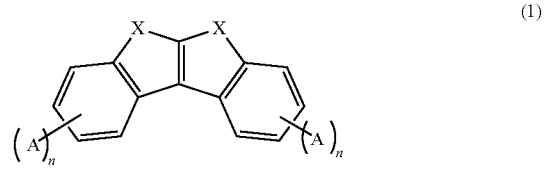

(1)

17 Claims, 4 Drawing Sheets

(51) Int. Cl.
*C07D 495/04* (2006.01)
*C07D 517/04* (2006.01)
*H01L 51/05* (2006.01)
*H01L 51/50* (2006.01)

(52) U.S. Cl.
CPC .......... *C07D517/04* (2013.01); *H01L 51/0068* (2013.01); *H01L 51/0073* (2013.01); *C09K 2211/1059* (2013.01); *C09K 2211/1088* (2013.01); *C09K 2211/1092* (2013.01); *H01L 51/0061* (2013.01); *H01L 51/0067* (2013.01); *H01L 51/0072* (2013.01); *H01L 51/0545* (2013.01); *H01L 51/5012* (2013.01); *Y02E 10/549* (2013.01)

(56) References Cited

OTHER PUBLICATIONS

Banihashemi, Ahmad et al., "Novel aromatic polyimides derived from benzofuro[2,3-b]benzofuran-2,3,8,9-tetracarboxylic dianhydride (BBTDA)", European Polymer Journal, 2004, vol. 40, pp. 1629-1635.

Banihashemi, Ahmed et al., "Synthesis and characterization of new thermally stable polybenzimidazoles and poly(amide-benzimidazole)s", European Polymer Journal, 2002, vol. 38, pp. 2119-2124.

Elmaleh, D. et al., "Reactions of 1,1-Diarylethylenes with Selenium Compounds", J. Chem. Soc. (C): Org., 1971, pp. 2637-2640.

Patai, S. et al., "Synthesis of Benzoselenopheno[2,3-b]benzoselenophens from 1,1-Diarylethylenes and Selenium Oxychloride", Journal of the Chemical Society, 1962, pp. 734-739.

* cited by examiner

CHALCOGEN-CONTAINING AROMATIC COMPOUND, ORGANIC SEMICONDUCTOR MATERIAL, AND ORGANIC ELECTRONIC DEVICE

TECHNICAL FIELD

The present invention relates to a novel chalcogen-containing aromatic compound and an organic electronic device using the compound, and to a light-emitting device, a thin-film transistor, and a photovoltaic device each utilizing the compound as an organic semiconductor material.

BACKGROUND ART

In recent years, an organic electronic device using an organic compound as a semiconductor material has been showing remarkable development. Representative examples of its application include: an organic electroluminescence device (organic EL device) expected as a new-generation flat panel display; an organic thin-film transistor (organic TFT) that has been attracting attention because the transistor enables the production of a thin-film transistor to be used for, for example, the driving of a pixel of a display by a low-cost process such as printing and can correspond to a flexible substrate; and a photovoltaic device (organic thin-film solar cell) as a light-weight, flexible power source.

In general, a high-temperature process and a high-vacuum process are essential for the formation of a semiconductor device using silicon that is an inorganic semiconductor material into a thin film. The high-temperature process is needed and hence silicon cannot be formed into a thin film on a plastic substrate or the like. Accordingly, it has been difficult to impart flexibility to a product into which the semiconductor device is incorporated or to reduce the weight of the product. In addition, the high-vacuum process is needed, and hence an increase in area of the product into which the semiconductor device is incorporated and the reduction of a cost for the product have been difficult.

The use of an organic compound as a semiconductor material has been expected to realize a low-price device because the organic compound can be easily processed as compared with silicon that is an inorganic substance. In addition, various substrates including a plastic substrate can be applied to a semiconductor device using the organic compound because the device can be produced at low temperatures. Further, the semiconductor material made of the organic compound is structurally flexible, and hence the combined use of the plastic substrate and the semiconductor material made of the organic compound has been expected to realize applications to organic semiconductor products taking advantage of such characteristics, e.g., devices including flexible displays such as an organic EL panel and electronic paper, liquid crystal displays, information tags, and large-area sensors such as an electronic artificial skin sheet and a sheet-type scanner.

An organic semiconductor material to be used in any such organic electronic device has been required to improve the luminous efficiency of an organic EL device, to lengthen its lifetime, and to reduce the voltage at which the device is driven, to reduce the threshold voltage of an organic TFT device and to increase a charge mobility for, for example, increasing its switching speed, and to improve the photoelectric conversion efficiency of an organic thin-film solar cell.

For example, a host material that serves to transport charge in a light-emitting layer is important for improving luminous efficiency in a material for an organic EL device. Typical examples of the host materials proposed include 4,4'-bis(9-carbazolyl)biphenyl (hereinafter referred to as "CBP") as a carbazole compound disclosed in Patent Literature 1 and 1,3-dicarbazolyl benzene (hereinafter referred to as "mCP") disclosed in Non Patent Literature 1. When CBP is used as a host material for a green phosphorescent light-emitting material typified by a tris(2-phenylpyridine) iridium complex (hereinafter referred to as "Ir(ppy)$_3$") the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)$_3$ lowers. Meanwhile, mCP shows a relatively good light-emitting characteristic when used as a host material for a blue phosphorescent light-emitting material represented by a bis[2-(4,6-difluorophenyl)pyridinato-N,C2'](picolinato)iridium complex (hereinafter referred to as "FIrpic"), but is not satisfactory in practical use particularly from the viewpoint of durability.

As described above, a host material in which injecting/transporting characteristics for both charges (a hole and an electron) are balanced is needed for obtaining high luminous efficiency in an organic EL device. Further, a compound that is electrochemically stable, and has high heat resistance and excellent amorphous stability has been desired, and hence additional improvements have been required.

In addition, among materials for organic TFT devices, an organic semiconductor material having charge-transporting property comparable to that of amorphous silicon has been reported in recent years. For example, the same level of charge mobility as that of the amorphous silicon has been reported in an organic TFT using, as an organic semiconductor material, pentacene that is a hydrocarbon-based, acene-type, polycyclic aromatic molecule in which five benzene rings are linearly fused introduced in Non Patent Literature 2. However, the use of pentacene as an organic semiconductor material for an organic TFT is disadvantageous from the viewpoints of an increase in area, flexibility, a reduction in weight, and a reduction in cost because an organic semiconductor thin-film layer is formed by a deposition method in an ultrahigh vacuum. In addition, Patent Literature 2 proposes a method of forming a pentacene crystal in a dilute solution of o-dichlorobenzene without employing a vacuum deposition method, but the production method is difficult and hence a stable device has not been obtained yet. The fact that the hydrocarbon-based, acene-type, polycyclic aromatic molecule like pentacene has low oxidation stability has also been pointed out as a problem.

In addition, researches on an organic thin-film solar cell have been initially progressed on the basis of a single-layer film using a merocyanine dye or the like. However, since the discovery of the fact that the formation of a multilayer film having a p layer for transporting an electron and an n layer for transporting a hole improves the efficiency with which optical input is converted into electrical output (photoelectric conversion efficiency), the multilayer film has been going mainstream. Materials used at the initiation of an investigation on the multilayer film were copper phthalocyanine (CuPC) for the p layer and peryleneimides (PTCBI) for the n layer. Meanwhile, in an organic thin-film solar cell using a polymer, researches have been conducted mainly on the so-called bulk heterostructure in which a conductive polymer is used as a material for the p layer, a fullerene (C60) derivative is used as a material for the n layer, and the materials are mixed and heat-treated to induce micro-layer separation, thereby increasing a hetero interface and improving the photoelectric conversion efficiency. Material systems used here were mainly a poly-3-hexylthiophene (P3HT) as a material for the p layer and a C60 derivative (PCBM) as a material for the n layer.

As described above, little headway has been made in a material for each layer of an organic thin-film solar cell since the early days, and a phthalocyanine derivative, a perylene-imide derivative, or a C60 derivative has still been used. Therefore, with a view to improving the photoelectric conversion efficiency, the development of a novel material that replaces those conventional materials has been earnestly desired. For example, Patent Literature 3 discloses an organic thin-film solar cell using a compound having a fluoranthene skeleton but the cell does not provide satisfactory photoelectric conversion efficiency.

In addition, Patent Literatures 4 and 5 each disclose, as an organic electronic device using a compound related to the present invention, an organic EL device using such a compound having a [3,2-b]-fused benzochalcogenophene skeleton as shown below. However, none of those literatures discloses a [2,3-b]-fused chalcogen-containing aromatic compound and its utility.

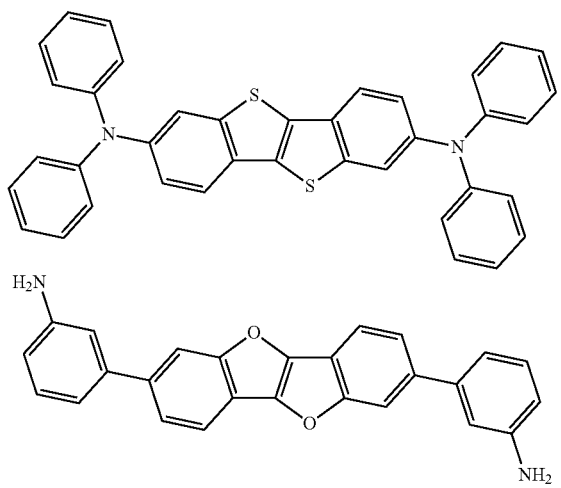

CITATION LIST

Patent Literature

[PTL 1] JP 2001-313178 A
[PTL 2] WO 2003/01659 A1
[PTL 3] JP 2009-290091 A
[PTL 4] JP 2009-246139 A
[PTL 5] JP 2009-246140 A

Non Patent Literature

[NPL 1] Applied Physics Letters, 2003, 82, 2422-2424
[NPL 2] Journal of Applied Physics, 2002, 92, 5259-5263

SUMMARY OF INVENTION

An object of the present invention is to provide a chalcogen compound having a high charge-transferring characteristic to be suitably used in an organic electronic device such as an organic EL panel, a liquid crystal display, an organic field-effect transistor, or an organic thin-film solar cell, and an organic electronic device using the compound.

As a result of extensive studies, the inventors of the present invention have found that a charge mobility increases when a chalcogen-containing aromatic compound having a specific structure is used as an organic semiconductor material in an organic electronic device, and have completed the present invention.

The present invention relates to a chalcogen-containing aromatic compound, which is represented by the general formula (1).

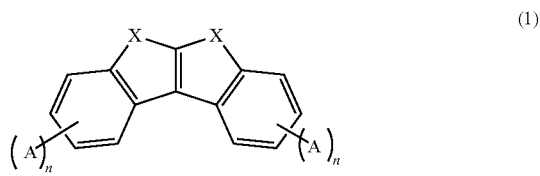

In the general formula (1), X's each independently represent oxygen, sulfur, or selenium, A's each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, an aromatic heterocyclic group having 3 to 50 carbon atoms and free of a fused heterocycle having 4 or more rings, or an amino group having 2 to 30 carbon atoms, and n's each independently represent an integer of 0 to 2, provided that a sum of two n's is 1 to 4.

Of the compounds each represented by the general formula (1), a compound in which X represents oxygen or sulfur is given as a preferred compound.

In addition, the present invention relates to an organic semiconductor material containing the chalcogen-containing aromatic compound.

In addition, the present invention relates to an organic electronic device using the organic semiconductor material.

DESCRIPTION OF EMBODIMENTS

Figure 1:
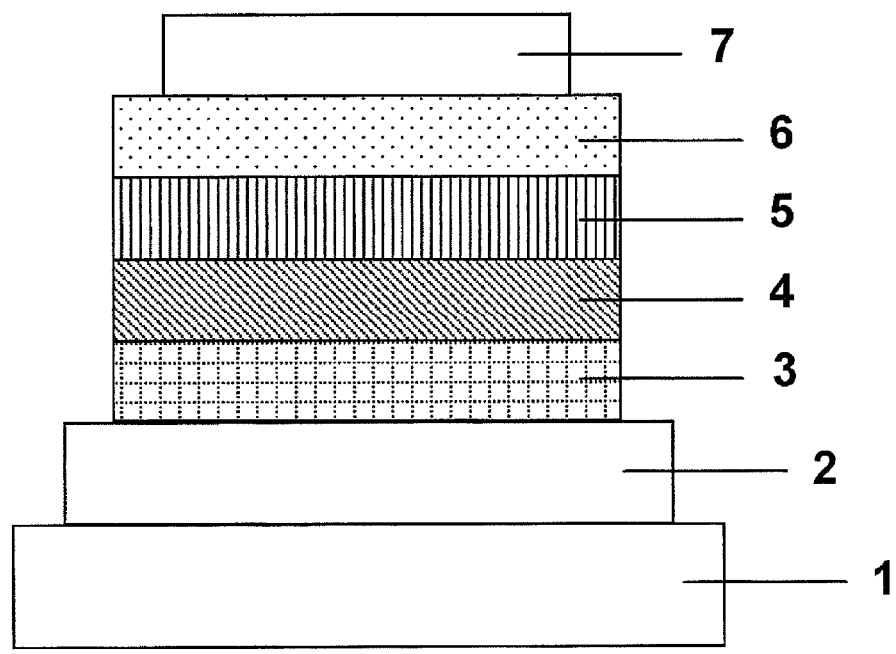
FIG. 1 is a schematic sectional view illustrating an example of the structure of an organic EL device.

A chalcogen-containing aromatic compound of the present invention is represented by the general formula (1). Hereinafter, the chalcogen-containing aromatic compound of the present invention is referred to as "compound of the present invention" or "compound represented by the general formula (1)."

In the general formula (1), X's each independently represent oxygen, sulfur, or selenium. It is preferred that X's each independently represent oxygen or sulfur. It is more preferred that X's each represent oxygen or sulfur, and two X's be identical to each other.

In the general formula (1), A's each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, an aromatic heterocyclic group having 3 to 50 carbon atoms and free of a fused heterocycle having 4 or more rings, or an amino group having 2 to 30 carbon atoms. It is preferred that A's each represent an alkyl group having 1 to 20 carbon atoms, a cycloalkyl group having 3 to 20 carbon atoms, an alkenyl group having 2 to 20 carbon atoms, an alkynyl group having 2 to 30 carbon atoms, an aromatic hydrocarbon group having 6 to 30 carbon atoms, an aromatic heterocyclic group having 3 to 30 carbon atoms and free of a fused heterocycle having 4 or more rings, or an amino group having 2 to 20 carbon atoms.

When A represents an alkyl group having 1 to 30 carbon atoms, the number of carbon atoms of the group is preferably 1 to 20, more preferably 1 to 10. Specific examples of the alkyl group in the case of having no substitution include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. The alkyl group may be linear or branched.

The alkyl group may have a substituent, and when the group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When the alkyl group has a substituent, the total number of substituents is 1 to 10. The number is preferably 1 to 6, more preferably 1 to 4. In addition, when the group has two or more substituents, the substituents may be identical to or different from each other.

In the description, in the calculation of the number of carbon atoms, when the group has a substituent, the number of carbon atoms of the substituent is also included.

When A represents a cycloalkyl group having 3 to 30 carbon atoms, the number of carbon atoms of the group is preferably 3 to 20, more preferably 5 to 10. Specific examples of the cycloalkyl group in the case of having no substitution include a cyclopropyl group, a cyclobutyl group, a cyclopentyl group, a cyclohexyl group, a cycloheptyl group, a cyclooctyl group, cyclohexyl group, and decahydronaphthyl group. Preferred examples thereof include a cyclopentyl group and a cyclohexyl group.

The cycloalkyl group may have a substituent, and when the group has a substituent, the substituent is an alkyl group having 1 to 10 carbon atoms, an aromatic hydrocarbon group having 6 to 18 carbon atoms, or an aromatic heterocyclic group having 3 to 18 carbon atoms.

When the cycloalkyl group has a substituent, the total number of substituents is 1 to 10. The number is preferably 1 to 6, more preferably 1 to 4. In addition, when the group has two or more substituents, the substituents may be identical to or different from each other.

When A represents an alkenyl group having 2 to 30 carbon atoms or an alkynyl group having 2 to 30 carbon atoms, the number of carbon atoms of the group is preferably 2 to 20, more preferably 2 to 10. Specific examples of the alkenyl group and the alkynyl group in the case of having no substitution include an ethylenyl group, a propylenyl group, a butenyl group, a pentenyl group, a hexenyl group, a heptenyl group, an octenyl group, an acetylenyl group, a propynyl group, a butynyl group, and a pentynyl group. Preferred examples thereof include an ethylenyl group, a propylenyl group, a butenyl group, an acetylenyl group, and a propynyl group. The alkenyl group and the alkynyl group may be linear or branched.

The alkenyl group or the alkynyl group may have a substituent, and when any such group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When A represents an aromatic hydrocarbon group having 6 to 50 carbon atoms, the number of carbon atoms of the group is preferably 6 to 30, more preferably 6 to 18. When A represents an aromatic heterocyclic group having 3 to 50 carbon atoms, the number of carbon atoms of the group is preferably 3 to 30, more preferably 3 to 18. Here, the aromatic heterocyclic group is free of a fused heterocycle having 4 or more rings.

Specific examples of the aromatic hydrocarbon group and the aromatic heterocyclic group in the case of having no substitution include a monovalent group produced by removing hydrogen from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphtene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, or an aromatic compound in which a plurality of such aromatic rings are linked to each other. Preferred examples thereof include a monovalent group produced by removing hydrogen from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, dibenzofuran, dibenzothiophene, or an aromatic compound in which a plurality of such aromatic rings are linked to each other.

It should be noted that in the case of the group produced from an aromatic compound in which a plurality of aromatic rings are linked to each other, the number of the aromatic rings to be linked to each other is preferably 2 to 10, more preferably 2 to 7, and the aromatic rings to be linked to each other may be identical to or different from each other. In that case, the bonding position of A to be bonded to nitrogen is not limited, and A may be bonded to a ring at a terminal portion of linked aromatic rings or may be bonded to a ring at the central portion thereof. Here, the term "aromatic ring" is a generic term for an aromatic hydrocarbon ring and an aromatic heterocycle. In addition, when the linked aromatic rings include at least one heterocycle, the linked aromatic rings are included in the category of the aromatic heterocyclic group.

Here, the monovalent group produced by the linking of a plurality of aromatic rings is, for example, represented by any one of the following formulae.

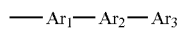  (11)

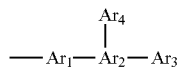  (12)

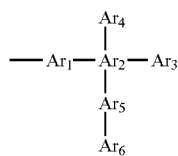  (13)

(In the formulae (11) to (13), $Ar_1$ to $Ar_6$ each represent a substituted or non-substituted aromatic ring.)

Specific examples of the group produced by the linking a plurality of aromatic rings include monovalent groups each produced by removing hydrogen from, for example, biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, or diphenylnaphthalene.

Here, the term "aromatic heterocyclic group free of a fused heterocycle having 4 or more rings" means a monocyclic aromatic heterocyclic group, or a fused aromatic heterocyclic group having 2 to 3 rings, and the aromatic heterocyclic group may have a substituent. It should be noted that when the aromatic heterocyclic group is, for example, such a group produced by the linking of a plurality of aromatic rings as represented by the formula (11), a monovalent or divalent aromatic heterocyclic group in the aromatic group is not a fused ring group having 4 or more rings.

The aromatic hydrocarbon group or the aromatic heterocyclic group may have a substituent, and when any such group has a substituent, the substituent is an alkyl group having 1 to 4 carbon atoms, a cycloalkyl group having 3 to 6 carbon atoms, an alkoxy group having 1 to 2 carbon atoms, an acetyl group, an amino group having 6 to 18 carbon atoms, a phosphanyl group having 6 to 18 carbon atoms, or a silyl group having 3 to 18 carbon atoms. The substituent is preferably an alkyl group having 1 to 4 carbon atoms, a cycloalkyl group having 3 to 6 carbon atoms, or an amino group having 6 to 15 carbon atoms. It should be noted that in this case, an aromatic group linked in a branched manner is not treated as a substituent.

When A represents an aromatic hydrocarbon group or an aromatic heterocyclic group, and the group has a substituent, the total number of substituents is 1 to 10. The number is preferably 1 to 6, more preferably 1 to 4. In addition, when the group has two or more substituents, the substituents may be identical to or different from each other.

When A represents an amino group having 2 to 30 carbon atoms, the amino group is represented by the following formula (4).

  (4)

In the formula (4), B's each independently represent an alkyl group having 1 to 10 carbon atoms, a cycloalkyl group having 3 to 11 carbon atoms, an aromatic hydrocarbon group having 6 to 18 carbon atoms, or an aromatic heterocyclic group having 3 to 18 carbon atoms. It is preferred that the B's each represent an alkyl group having 1 to 8 carbon atoms, a cycloalkyl group having 3 to 8 carbon atoms, an aromatic hydrocarbon group having 6 to 12 carbon atoms, or an aromatic heterocyclic group having 3 to 12 carbon atoms. Here, the aromatic heterocyclic group is free of a fused ring structure having 4 or more rings.

In the formula (4), the total number of carbon atoms in two B's is 30 or less. The total number is preferably 2 to 20, more preferably 6 to 20.

Specific examples of the case where the B's in the formula (4) each represent an alkyl group, a cycloalkyl group, an aromatic hydrocarbon group, or an aromatic heterocyclic group are identical to those of the alkyl group, cycloalkyl group, aromatic hydrocarbon group, or aromatic heterocyclic group constituting A except for a difference in total number of carbon atoms. In addition, description in the case of A holds true for the case where such alkyl group, cycloalkyl group, aromatic hydrocarbon group, or aromatic heterocyclic group has a substituent.

In the formula (4), B represents preferably a methyl group, an ethyl group, an isopropyl group, a phenyl group, a naphthyl group, a pyridyl group, or a quinolyl group, more preferably a phenyl group or a naphthyl group.

When B represents an aromatic hydrocarbon group or an aromatic heterocyclic group, any such group may have a substituent. When the group has a substituent, the substituent is an alkyl group having 1 to 4 carbon atoms, a cycloalkyl group having 3 to 6 carbon atoms, an alkoxy group having 1 to 2 carbon atoms, or an acetyl group.

In the general formula (1), n's each independently represent an integer of 0 to 2 but the sum of two n's is 1 to 4. It is preferred that n's each independently represent an integer of 1 or 2. It is more preferred that both n's each represent 1. That is, the sum of the integers represented by two n's is preferably 2 to 4, more preferably 2.

The compound of the present invention can be synthesized by employing a known approach after selecting a raw material in accordance with the structure of the target compound.

For example, when both X's in the general formula (1) each represent oxygen, for example, 2,9-dibromo[1]benzofuro[2,3-b]benzofuran can be synthesized by the following reaction formula with reference to a synthesis example described in The Journal of Organic Chemistry, 1990, 55, p. 1240.

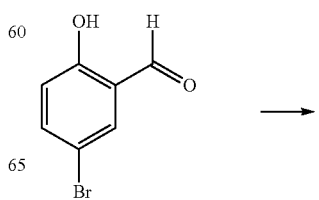

-continued

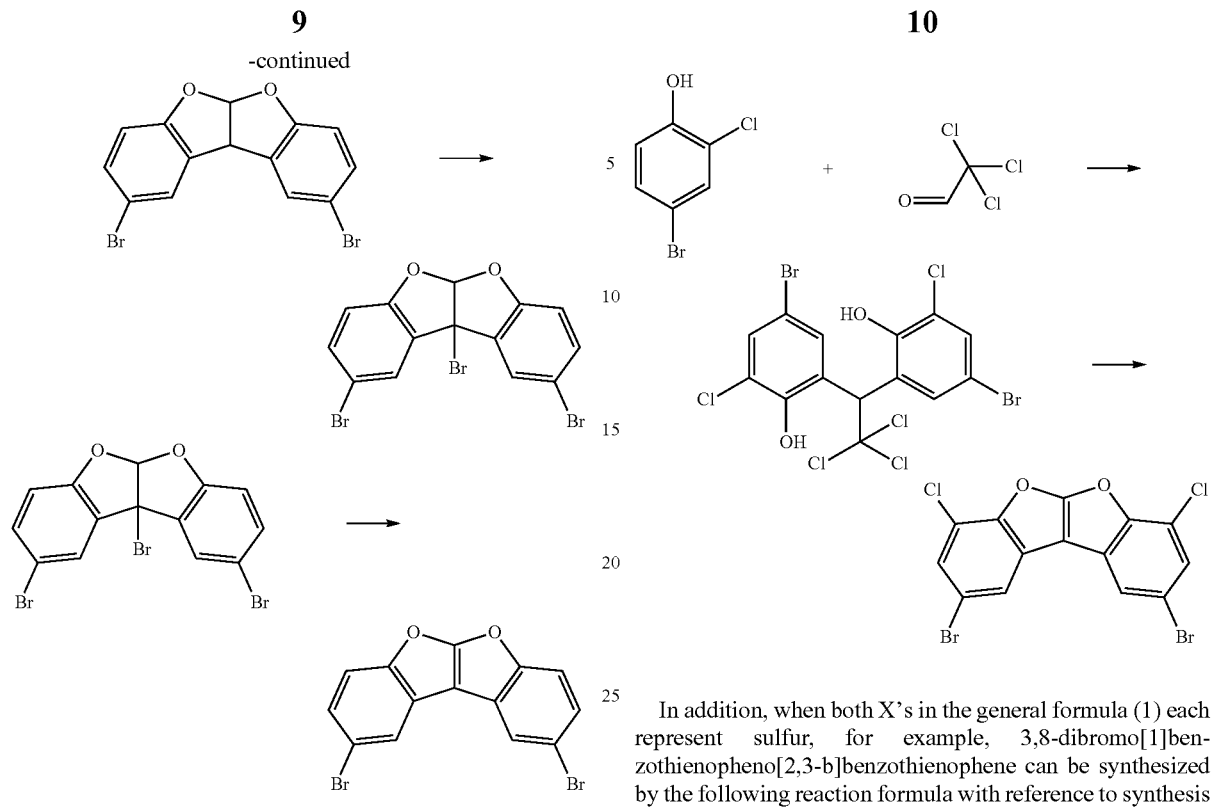

In addition, 3,8-dibromo[1]benzofuro[2,3-b]benzofuran that is another halogen material can also be synthesized by the same approach.

In addition, 2,9-dibromo-4,7-dichloro[1]benzofuro[2,3-b]benzofuran that is another halogen material can be synthesized by the following reaction formula with reference to a synthesis example described in Chemische Berichte, 1959, vol. 92, p. 900.

In addition, when both X's in the general formula (1) each represent sulfur, for example, 3,8-dibromo[1]benzothienopheno[2,3-b]benzothienophene can be synthesized by the following reaction formula with reference to synthesis examples described in Chemistry Letters, 2006, vol. 35, p. 422 and Journal of Scientific and Industrial Research, 1957, vol. 16B, p. 348.

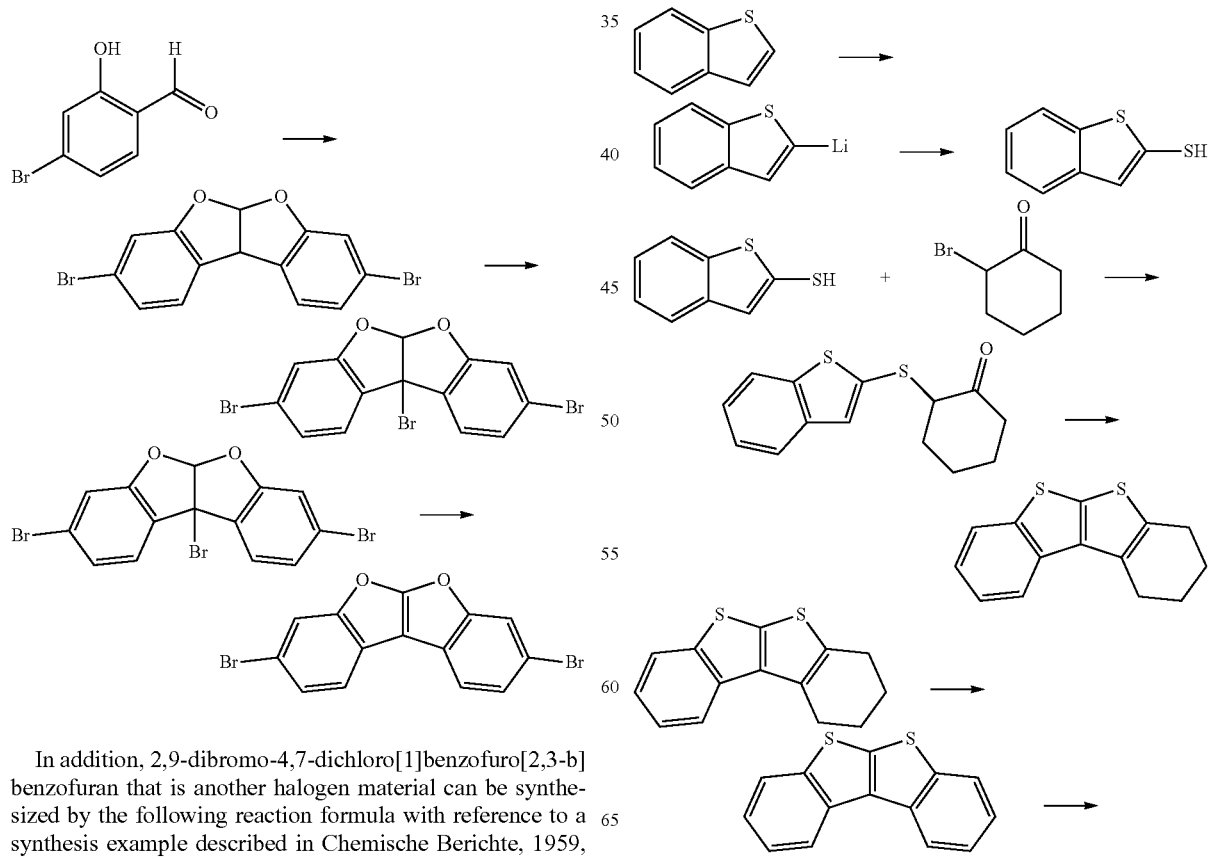

-continued

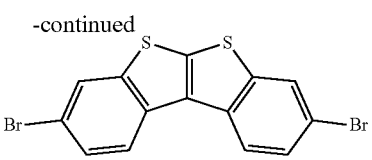

The compound of the present invention represented by the general formula (1) can be synthesized by substituting a halogen on a six-membered ring of each of the various compounds obtained by the foregoing reaction formulae with the corresponding substituent through a coupling reaction such as the Suzuki-Miyaura reaction or the Ullmann reaction.

Specific examples of the compound of the present invention represented by the general formula (1) are shown below. However, the compound of the present invention is not limited thereto.

(1-1)

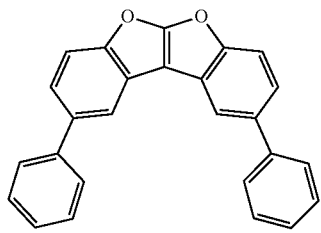

(1-2)

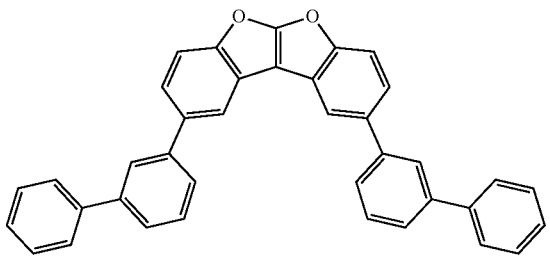

(1-3)

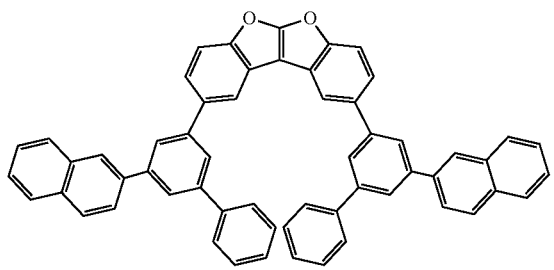

(1-4)

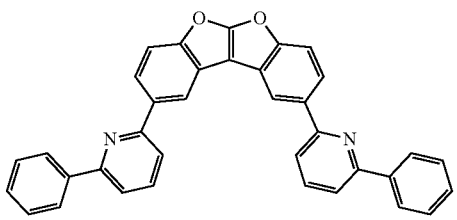

(1-5)

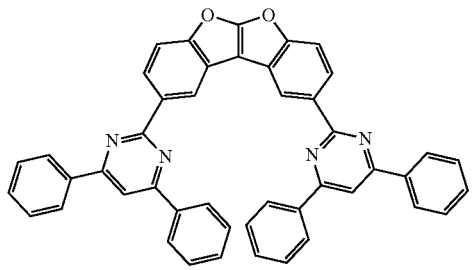

(1-6)

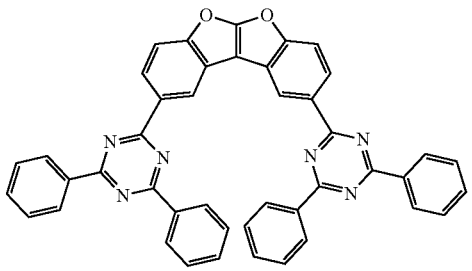

(1-7)

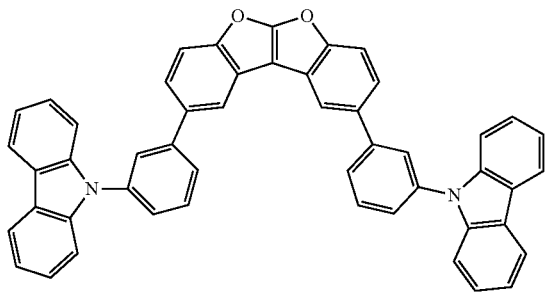

(1-8)

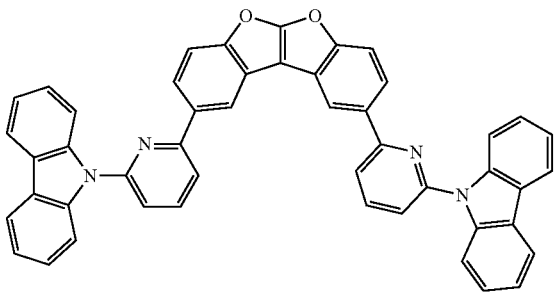

-continued
(1-9)
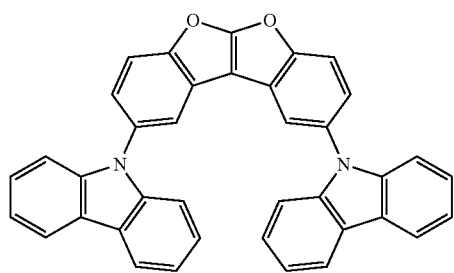
(1-10)
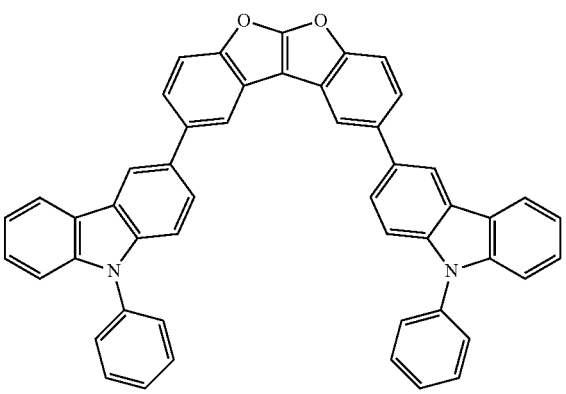
(1-11)
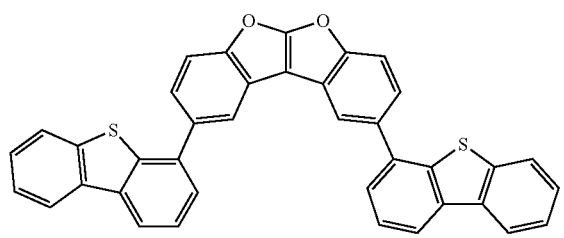
(1-12)
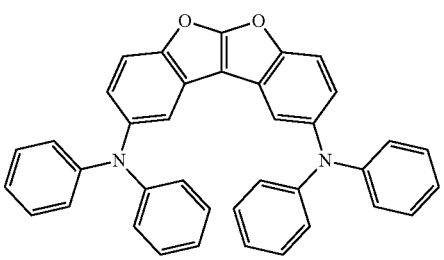
(1-13)
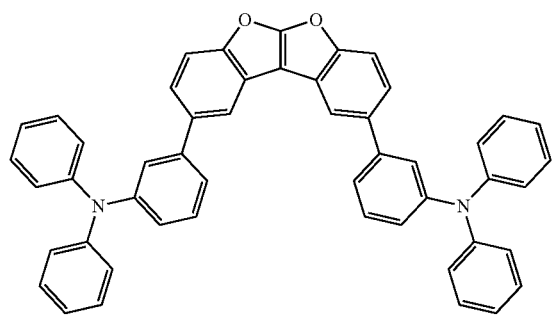
(1-14)
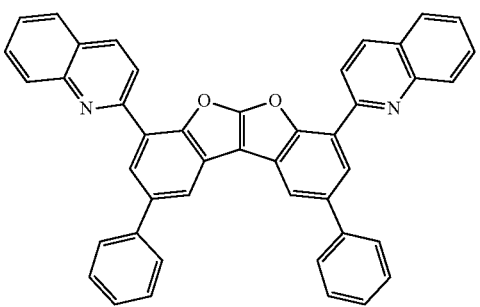
(1-15)
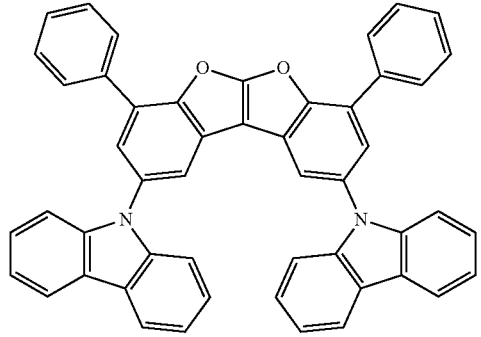
(1-16)
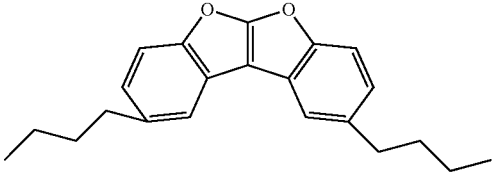
(1-17)
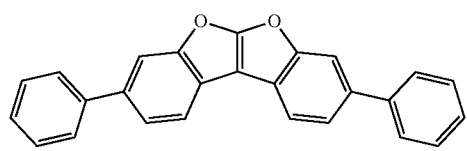
(1-18)
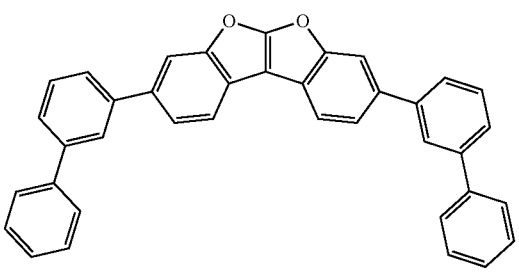

-continued
(1-19)
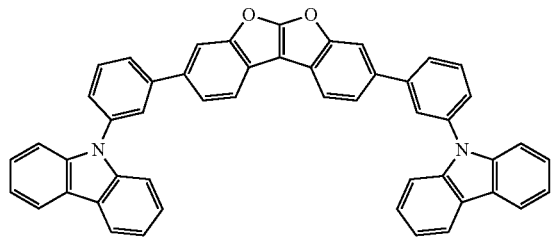
(1-20)
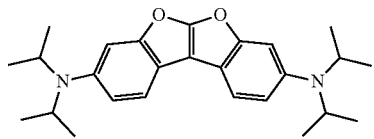
(1-21)
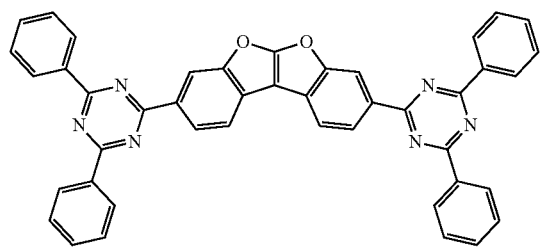
(1-22)
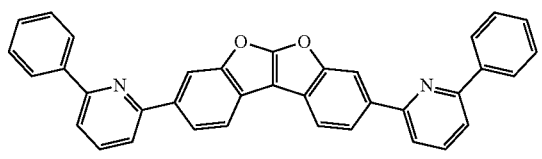
(1-23)
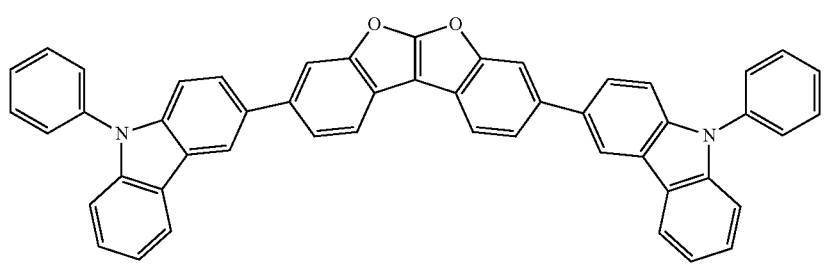
(1-24)
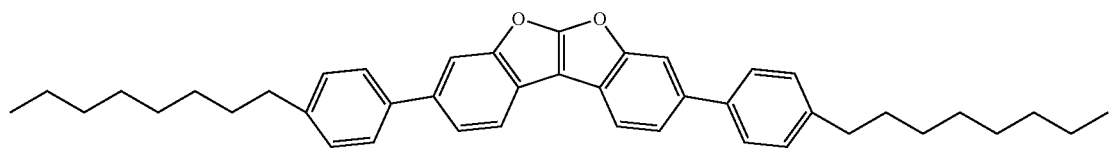
(1-25)
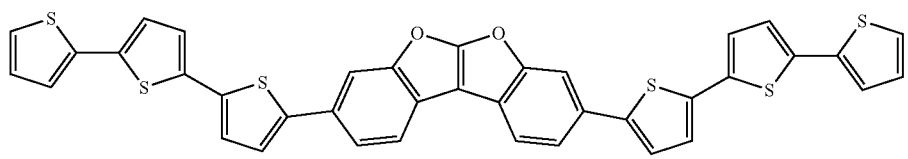
(1-26)
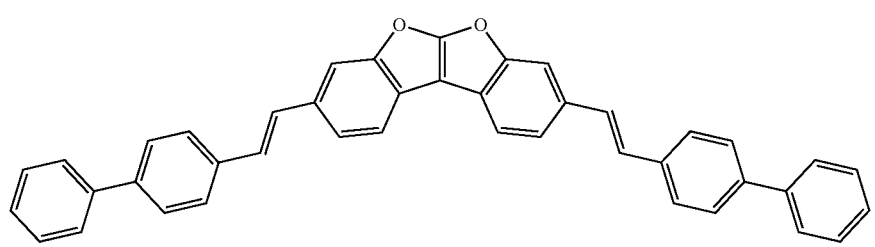

-continued
(2-1)
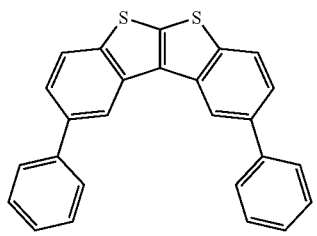
(2-2)
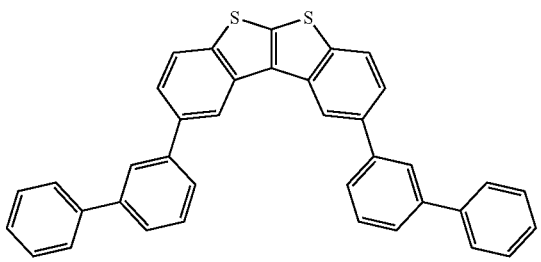
(2-3)
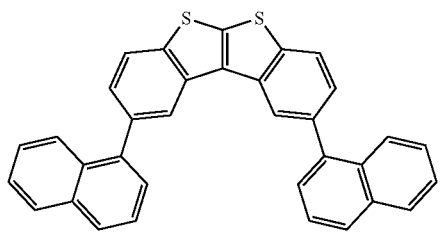
(2-4)
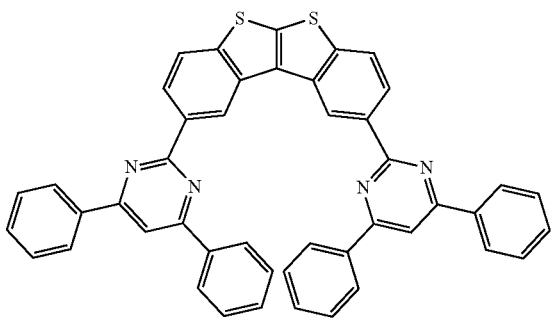
(2-5)
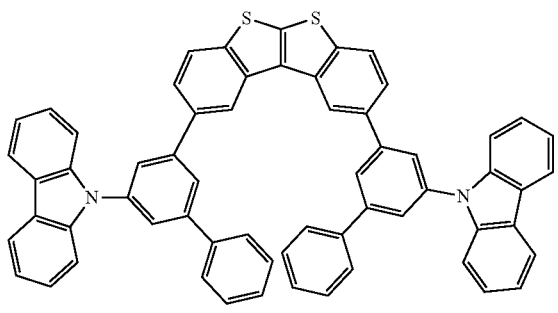
(2-6)
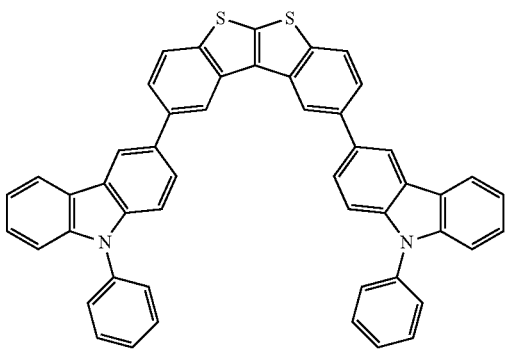
(2-7)
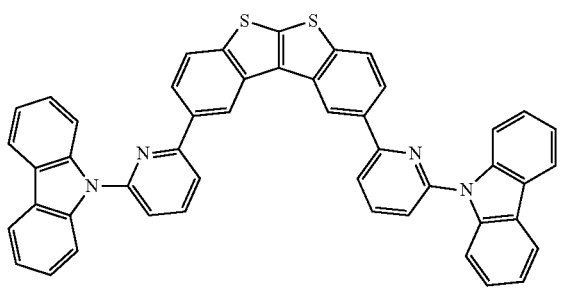
(2-8)
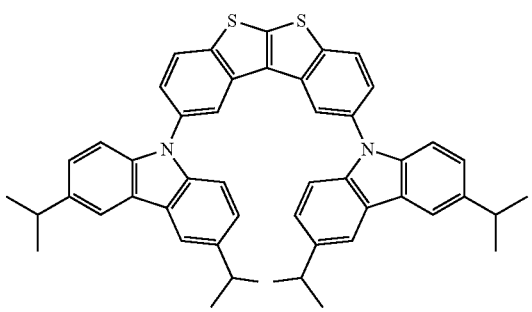
(2-9)
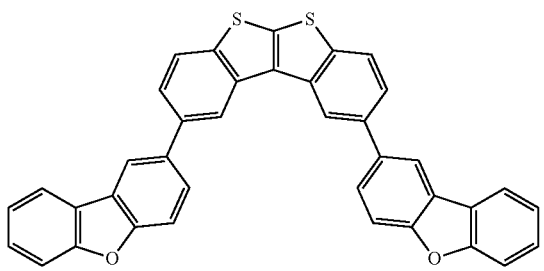
(2-10)
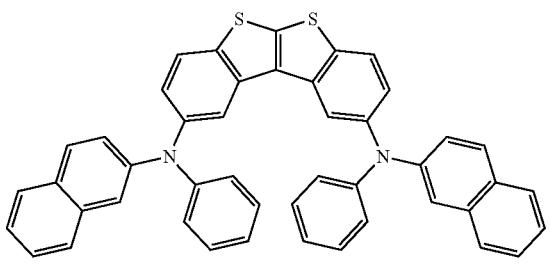

-continued
(2-11)
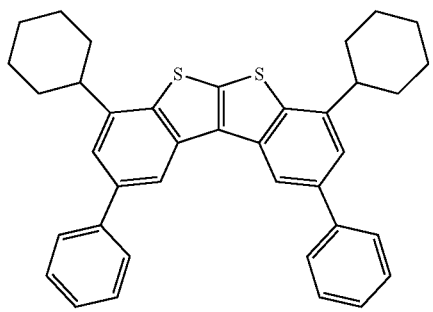
(2-12)
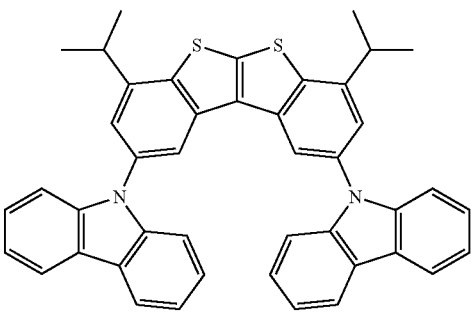
(2-13)
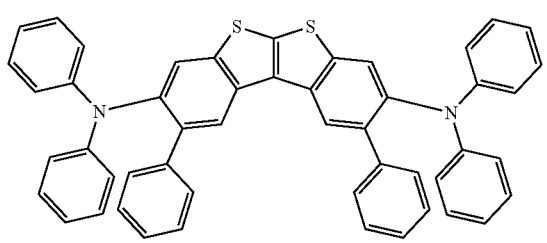
(2-14)
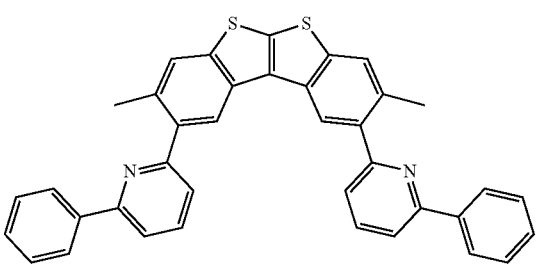
(2-15)
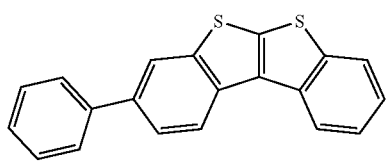
(2-16)
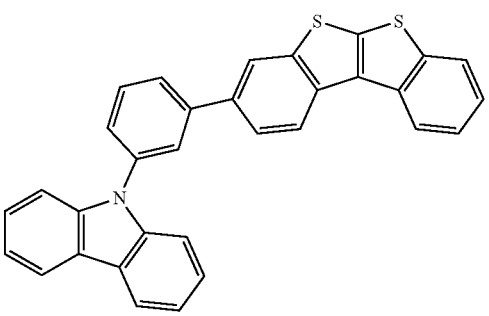
(2-17)
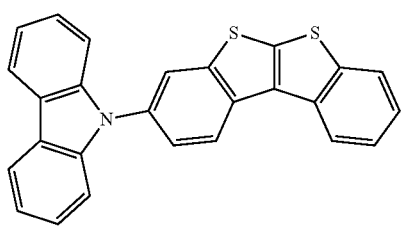
(2-18)
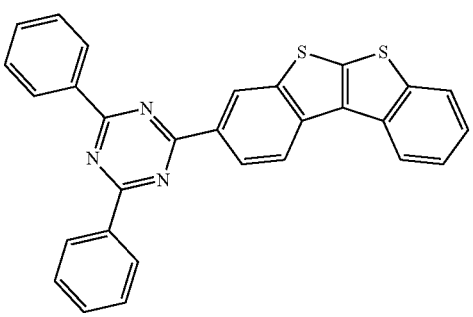
(2-19)
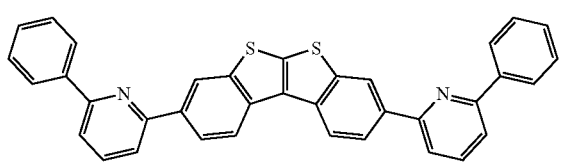
(2-20)
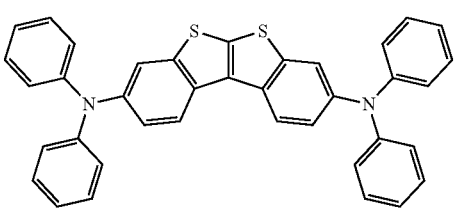

-continued
(2-21)
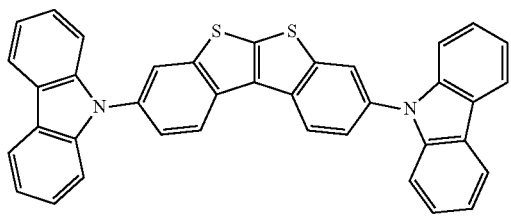
(2-22)
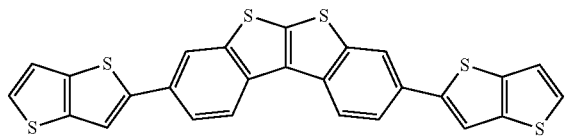
(2-23)
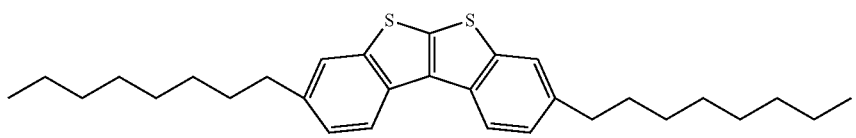
(2-24)
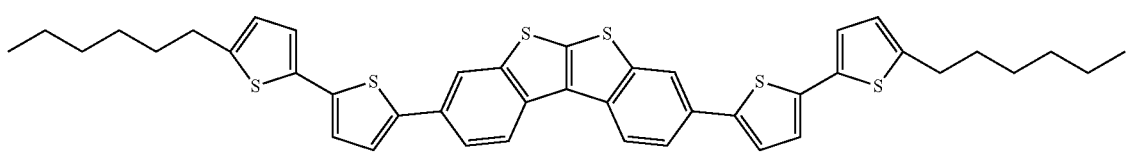
(2-25)
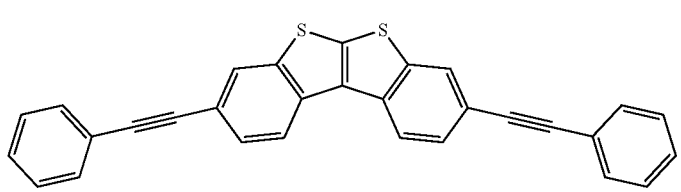
(2-26)
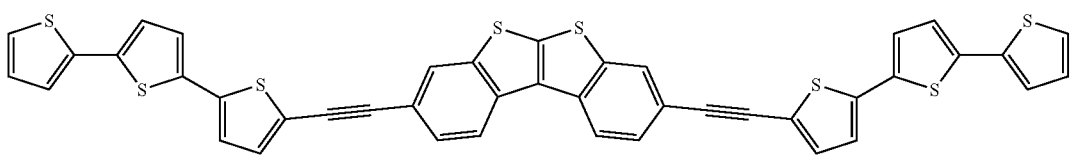
(3-1)
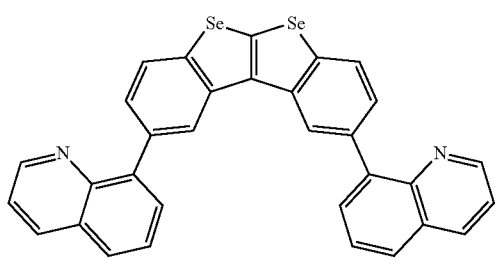
(3-2)
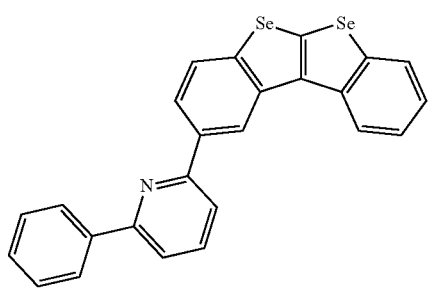
(3-3)
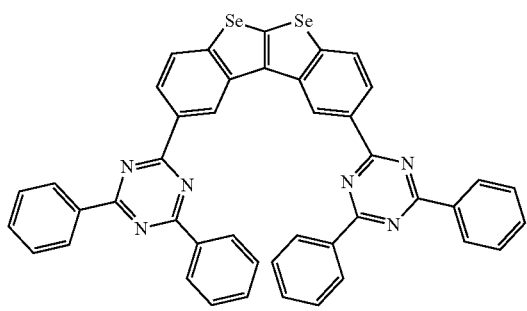
(3-4)
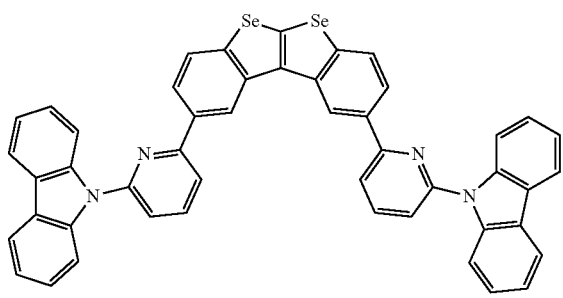

-continued
(3-5)
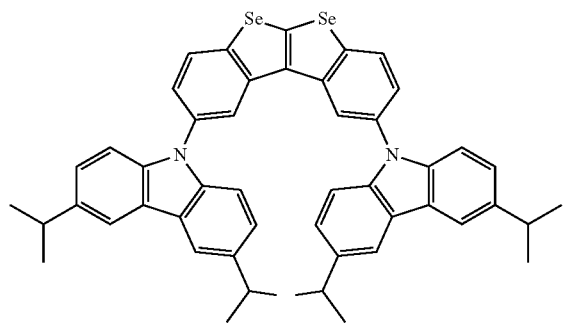
(3-6)
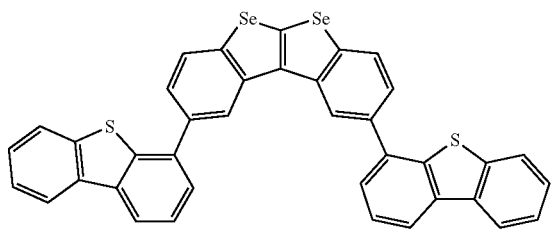
(3-7)
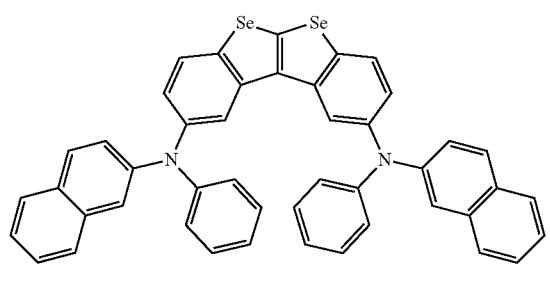
(3-8)
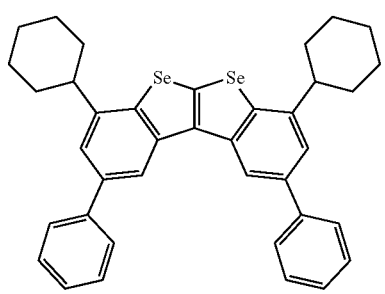
(3-9)
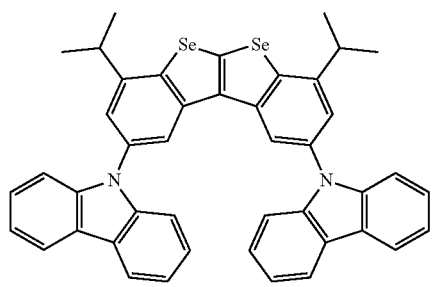
(3-10)
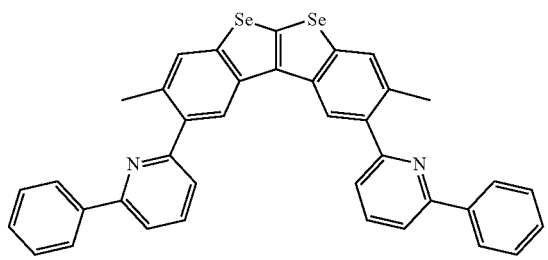
(4-1)
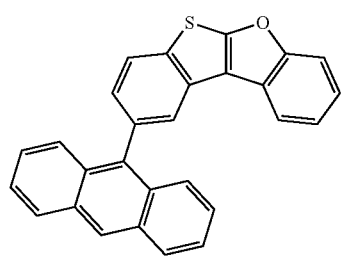
(4-2)
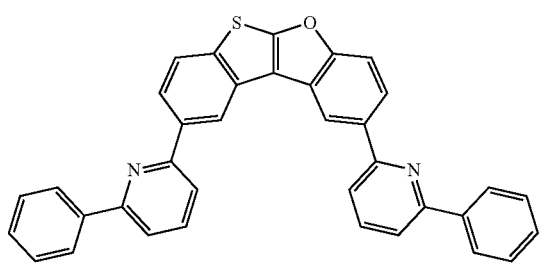
(4-3)
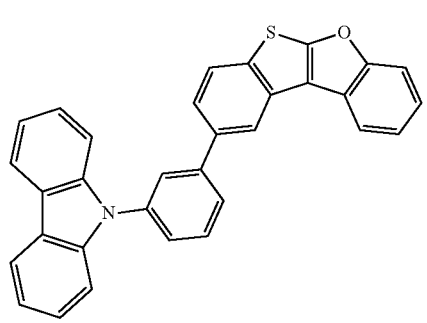
(4-4)
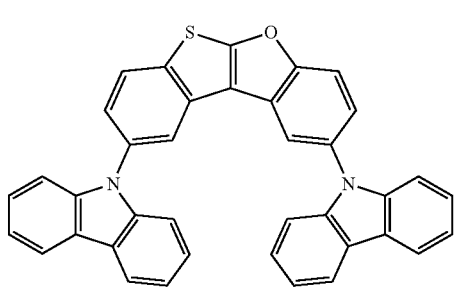

-continued
(4-5)
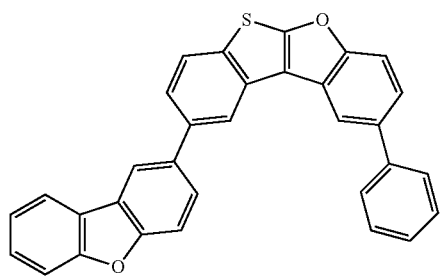
(4-6)
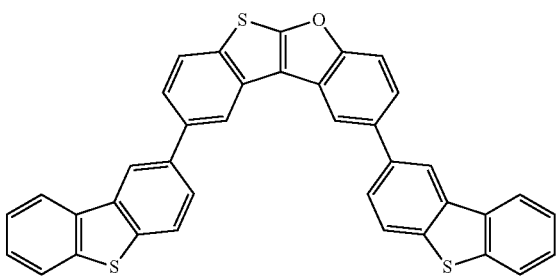
(4-7)
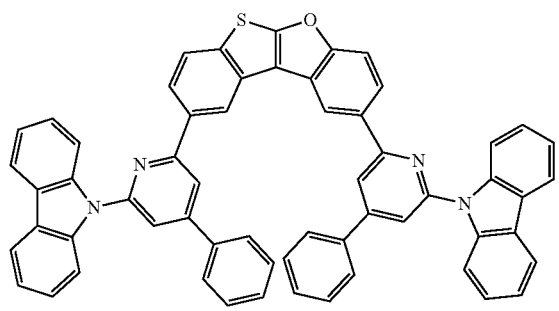
(4-8)
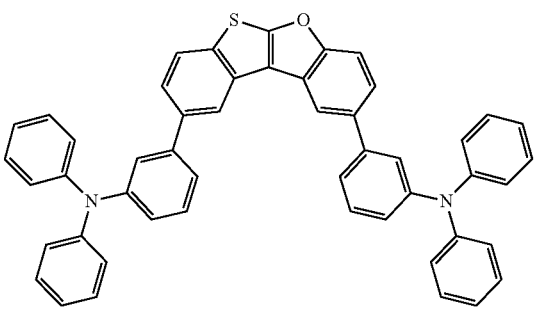
(4-9)
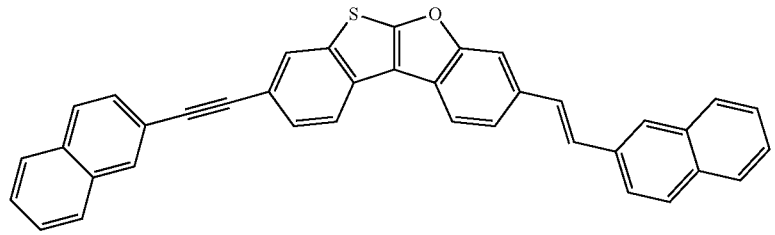
(4-10)
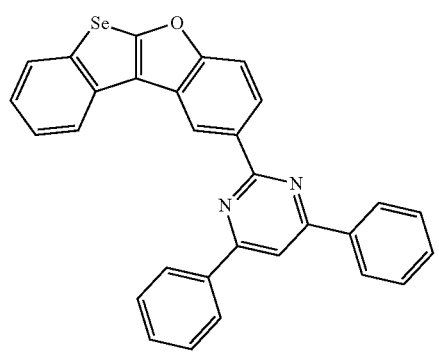
(4-11)
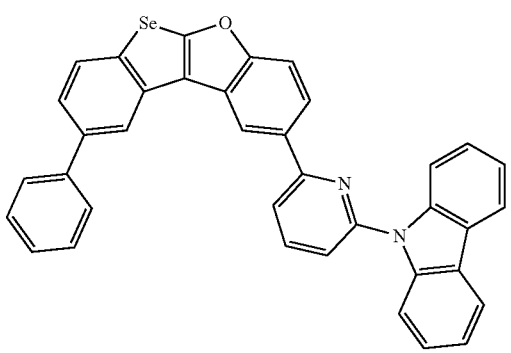
(4-12)
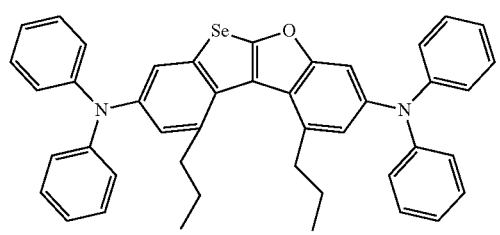
(4-13)
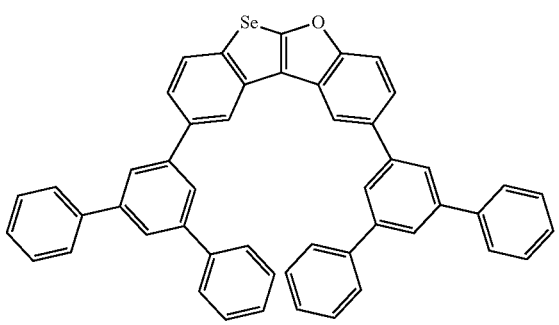

-continued
(4-14)
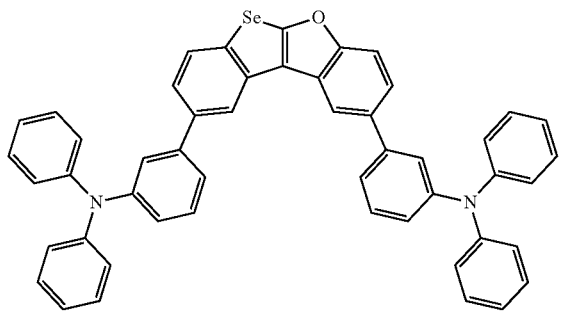
(4-15)
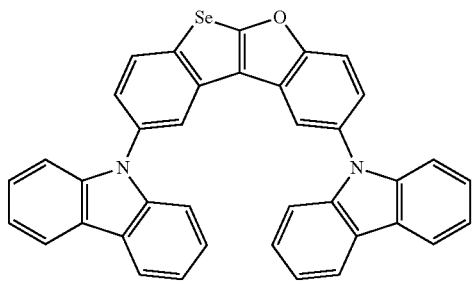
(4-16)
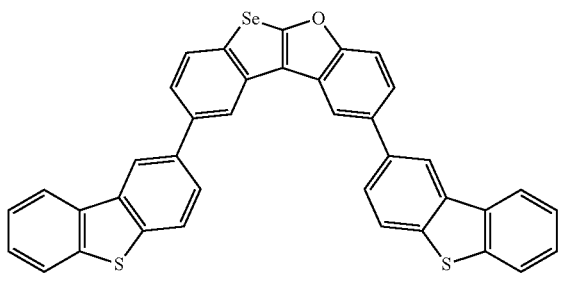
(4-17)
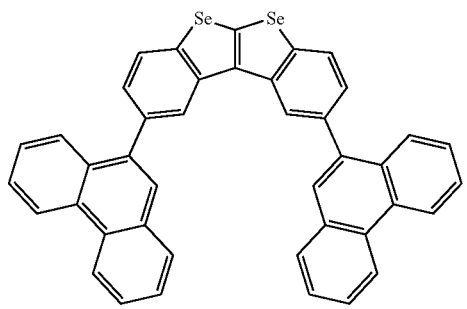
(4-18)
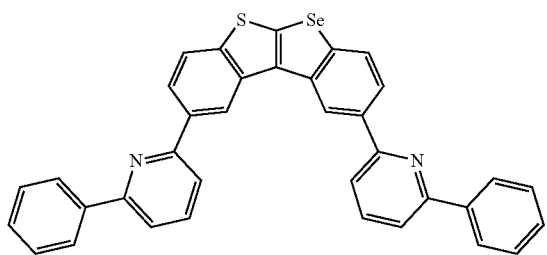
(4-19)
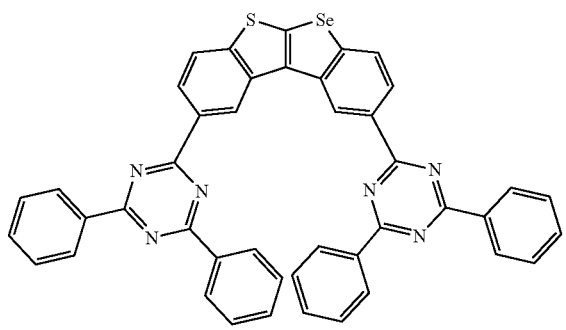
(4-20)
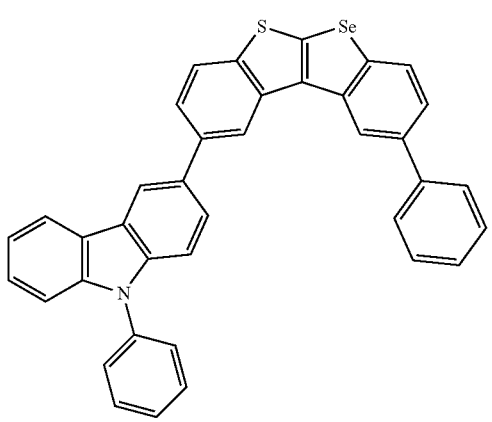
(4-21)
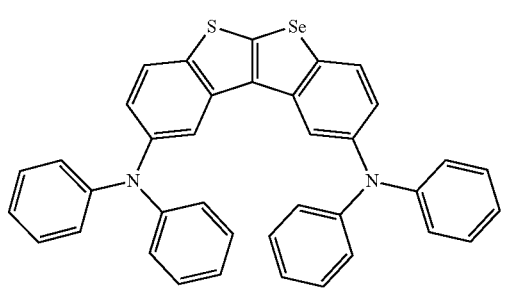

-continued (4-22)

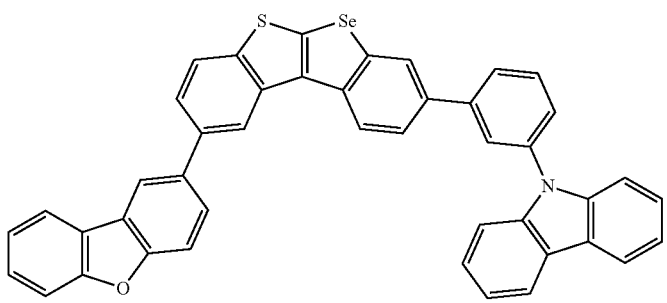

Next, an organic semiconductor material of the present invention and an organic electronic device of the present invention are described. The chalcogen-containing aromatic compound of the present invention is useful as an organic semiconductor material because the compound itself has a function as an organic semiconductor material. The organic semiconductor material of the present invention contains the nitrogen-containing aromatic compound of the present invention. The organic semiconductor material of the present invention has only to contain the compound of the present invention, and for example, may be used as a mixture with any other organic semiconductor material and may contain various dopants. Examples of the dopant which may be used in the case of using the organic semiconductor material in a light-emitting layer of an organic EL device include: coumarin-, quinacridone-, rubrene-, and stilbene-based derivatives; fluorescent dyes; and noble metal complexes such as an iridium complex and a platinum complex.

The organic electronic device of the present invention is an organic electronic device using the organic semiconductor material of the present invention. That is, the organic electronic device of the present invention is an organic electronic device containing the chalcogen-containing aromatic compound of the present invention. Specifically, the organic electronic device of the present invention has at least one organic layer and at least one layer of the organic layer contains the compound of the present invention.

Although the organic electronic device of the present invention can be used in various embodiments, a preferred embodiment is an organic EL device. Specifically, the organic electronic device is an organic electronic device formed of an organic EL device obtained by laminating, on a substrate, an anode, an organic layer including a light-emitting layer, and a cathode, in which the organic layer contains the compound of the present invention.

The structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

The compound of the present invention may be used for any of the layers in the organic EL device. The compound is preferably used for the light-emitting layer, the hole-transporting layer, the electron-blocking layer, the hole-blocking layer, or the electron-transporting layer, particularly preferably used for the light-emitting layer, the hole-transporting layer, or the electron-blocking layer.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 µm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred $\Omega/\square$ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred $\Omega/\square$ or less, and the thickness of the resultant film is selected from usually the range of 10 nm to 5 µm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer, which may be any one of a fluorescent light-emitting layer and a phosphorescent light-emitting layer, is preferably the phosphorescent light-emitting layer.

When the light-emitting layer is the fluorescent light-emitting layer, at least one kind of fluorescent light-emitting material may be used alone as a fluorescent light-emitting material, but it is preferred that the fluorescent light-emitting material be used as a fluorescent light-emitting dopant and a host material be incorporated.

Although the compound represented by the general formula (1) can be used as the fluorescent light-emitting material in the light-emitting layer, when the compound is used in any other organic layer, a material selected from fluorescent light-emitting materials known to the public by many patent literatures and the like can be used. Examples thereof include: a benzoxazole derivative, a benzimidazole derivative, a benzothiazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a cyclopentadiene derivative, a styrylamine derivative, a diketopyrrolopyrrole derivative, and an aromatic dimethylidyne compound; various metal complexes exemplified by a metal complex of an 8-quinolinol derivative and a metal complex, rare earth metal complex, or transition metal complex of a pyrromethene derivative; polymer compounds such as a polythiophene, a polyphenylene, and a polyphenylenevinylene; and an organic silane derivative. Preferred examples thereof include a fused aromatic compound, a styryl compound, a diketopyrrolopyrrole compound, an oxazine compound, and a metal complex, transition metal complex, or lanthanoid complex of pyrromethene. More preferable examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthophenanthridine, phenanthroxazole, quinolino[6,5-f]quinoline, and benzothiophanthrene. Each of those materials may have an aryl group, a heteroaromatic ring group, a diarylamino group, or an alkyl group as a substituent.

When the fluorescent light-emitting material is used as the fluorescent light-emitting dopant and the host material is incorporated, the amount of the fluorescent light-emitting dopant to be incorporated into the light-emitting layer desirably falls within the range of 0.01 to 20 wt %, preferably 0.1 to 10 wt %.

In ordinary cases, the organic EL device is caused to emit light by producing a light-emitting substance in an excited state through the injection of charge into a light-emitting substance from each of both electrodes, i.e., the anode and the cathode. It is said that in the case of a charge injection-type organic EL device, 25% of produced excitons are excited to excited singlet states and the remaining 75% are excited to excited triplet states. As described in the meeting proceedings (19p-ZK-4 and 19p-ZK-5) of the 57th Meeting of The Japan Society of Applied Physics and Related Societies, a specific fluorescent light-emitting substance is known to express thermally activated delayed fluorescence via the following mechanism. After the transition of its energy into an excited triplet state through intersystem crossing or the like, the substance undergoes inverse intersystem crossing into an excited singlet state by virtue of triplet-triplet annihilation or the absorption of a thermal energy, thereby radiating fluorescence. The organic EL device using the compound of the present invention can also express delayed fluorescence. In this case, the fluorescence can include both fluorescent emission and delayed fluorescent emission, provided that light emission from the host material may constitute part of the light emission.

In the case where the light-emitting layer is a phosphorescent light-emitting layer, a phosphorescent light-emitting dopant and a host material are incorporated. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and may be used.

Preferred examples of the phosphorescent light-emitting dopant include complexes such as Ir(ppy)₃ complexes such as (Bt)₂Iracac, and complexes such as (Btp)Ptacac, the complexes each having a noble metal element such as Ir as a central metal. Specific examples of those complexes are shown below, but the complexes are not limited to the compounds described below.

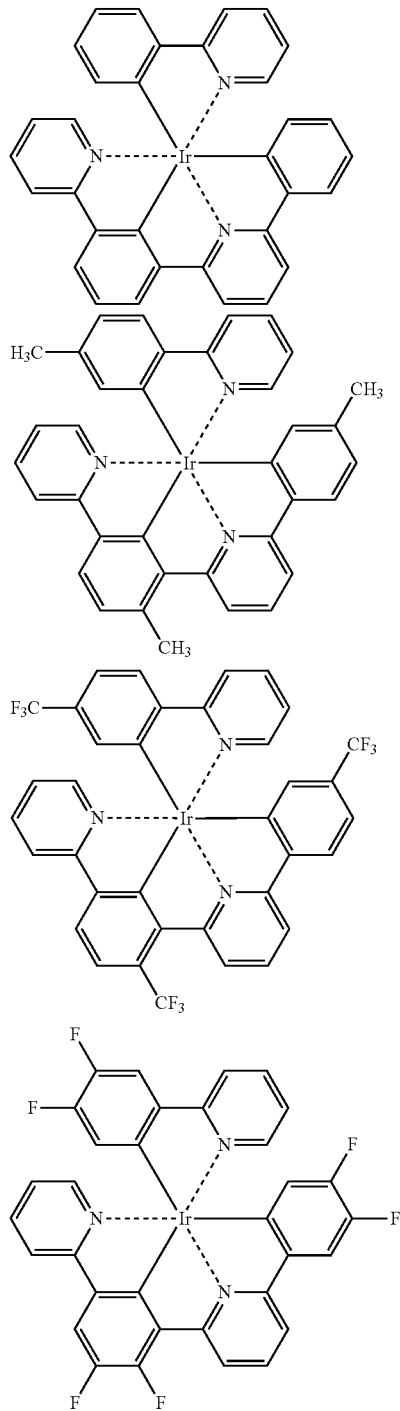

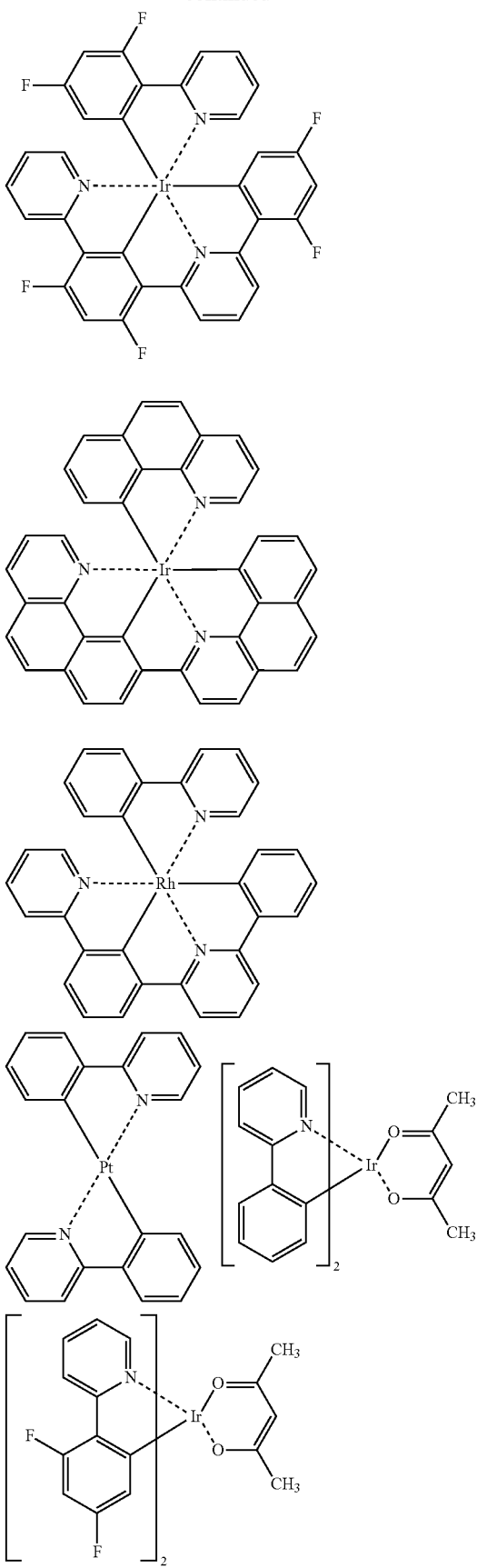

-continued
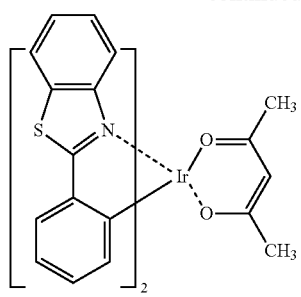
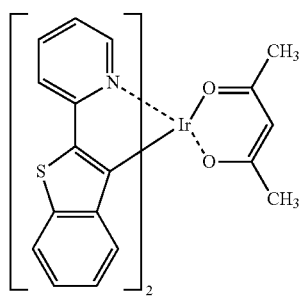
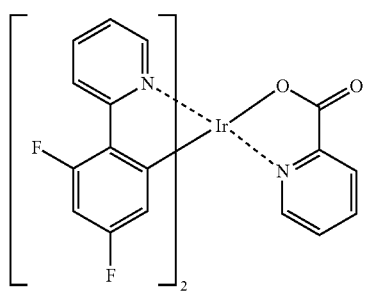
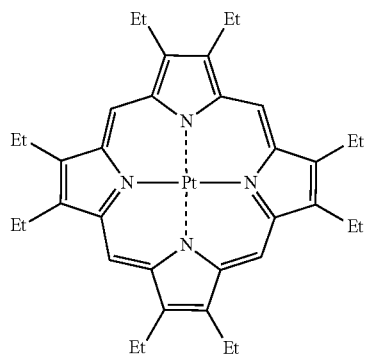
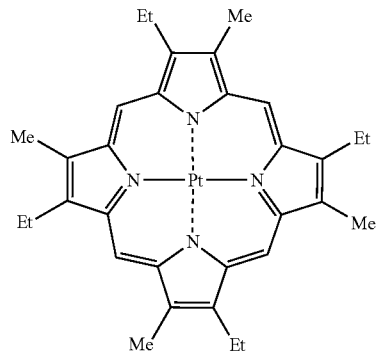
-continued
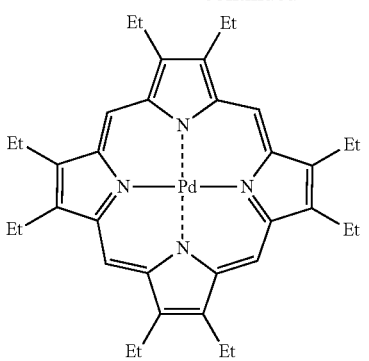
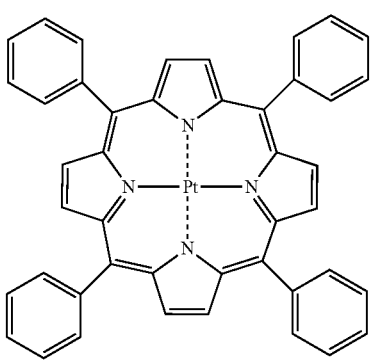
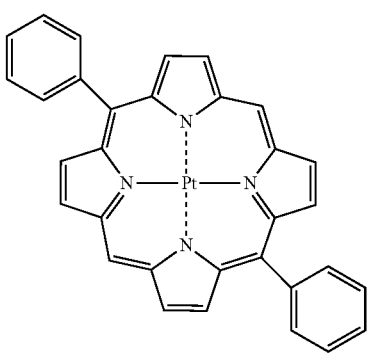
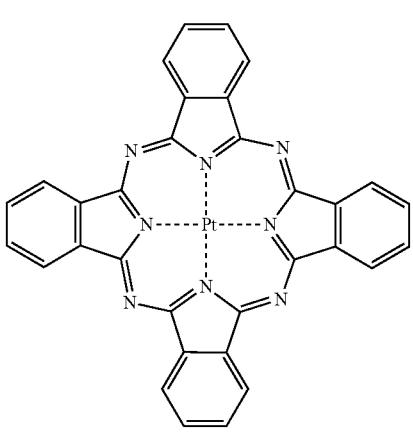

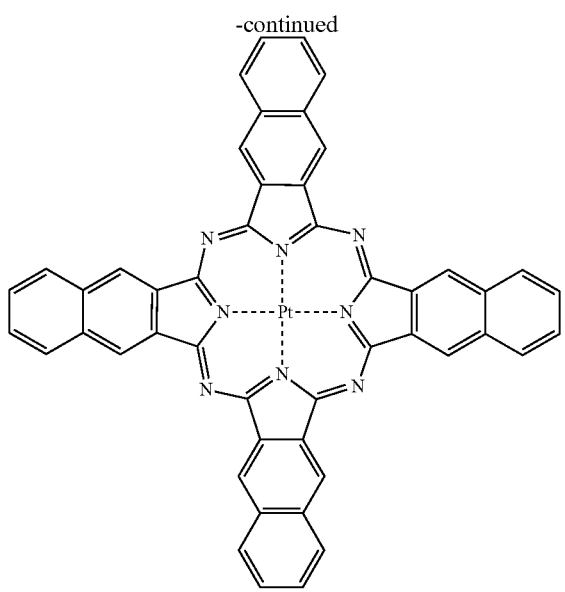

The content of the phosphorescent light-emitting dopant in the light-emitting layer is in the range of preferably 1 to 50 wt %, more preferably 5 to 30 wt %.

It is preferred to use, as a host material in the light-emitting layer, the compound of the present invention represented by the general formula (1). However, when the compound of the present invention is used in any of the organic layers other than the light-emitting layer, the material to be used in the light-emitting layer may be another host material other than the compound of the present invention, or the compound of the present invention and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence a suitable host material may be chosen from those in the patent literatures and the like. Specific examples of the host material, which are not particularly limited, include an indole derivative, a carbazole derivative, an indolocarbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquinone derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be provided as required. Although the compound of the present invention represented by the general formula (1) can be used as an injecting material, when the compound is used in any other organic layer, any compound selected from conventionally known compounds can be used.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the compound of the present invention represented by the general formula (1) for the hole-blocking layer. However, when the compound is used in any other organic layer, a known material for a hole-blocking layer may be used. Further, it is possible to use, as a material for the hole-blocking layer, any of the below-mentioned materials for the electron-transporting layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Although the compound of the present invention represented by the general formula (1) can be used as a material for the electron-blocking layer, when the compound is used in any other organic layer, any of the below-mentioned materials for the hole-transporting layer can be used as required. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the compound of the present invention represented by the general formula (1) can be used as a material for the exciton-blocking layer, when the compound is used in any other organic layer, any compound selected from conventionally known compounds can be used. Examples thereof include 1,3-dicarbazolylbenzene (mCP) and bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be provided.

The hole-transporting material has hole-injecting property or hole-transporting property or has electron-blocking property, and any of an organic compound and an inorganic compound may be used as the hole-transporting material. Although it is preferred to use the compound of the present invention represented by the general formula (1) for the hole-transporting layer, when the compound is used in any other organic layer, any compound selected from conventionally known compounds may be used. Examples of the known hole-transporting material which may be used include a triazole derivative, an oxadiazole derivative, an imidazole derivative, a polyarylalkane derivative, a pyrazoline derivative, and a pyrazolone derivative, a phenylenediamine derivative, an aromatic amine derivative, an amino-substituted chalcone derivative, an oxazole derivative, a styrylanthracene derivative, a fluorenone derivative, a hydrazone derivative, a stilbene derivative, a silazane derivative, an aniline-based copolymer, a porphyrin compound, a styrylamine compound, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be provided.

An electron-transporting material (which also serves as a hole-blocking material in some cases) has only to have a function of transferring electrons injected from the cathode into the light-emitting layer. Although it is preferred to use the compound of the present invention represented by the general formula (1) for the electron-transporting layer, when the compound is used in any other organic layer, any compound selected from conventionally known compounds may be used. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative which has a quinoxaline ring known as an electron withdrawing group. Further, it is also possible to use a polymer material in which any of those materials is introduced in a polymer chain or is used as a polymer main chain.

Another preferred embodiment of the organic electronic device containing the compound of the present invention is an organic TFT device. Specifically, the organic electronic device is an organic electronic device formed of an organic TFT device having, on a substrate, a gate electrode, a gate insulating layer, an organic semiconductor layer, a source electrode, and a drain electrode, in which the organic semiconductor layer contains the compound of the present invention.

The structure of the organic TFT device of the present invention is described with reference to the drawings but the structure of the organic TFT device of the present invention is by no means limited to those illustrated in the drawings.

Figure 2:
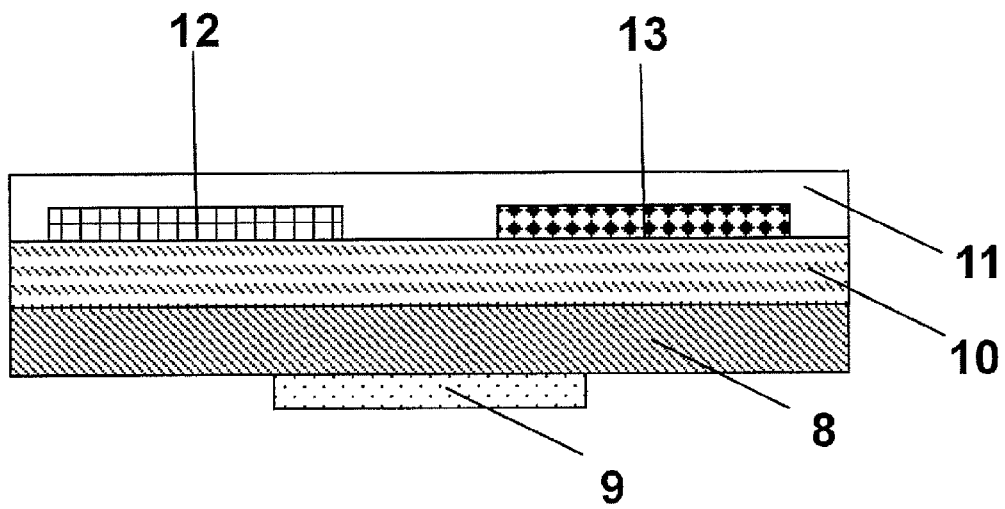
FIG. 2 illustrates a schematic sectional view illustrating an example of the structure of an organic TFT device.
Figure 3:
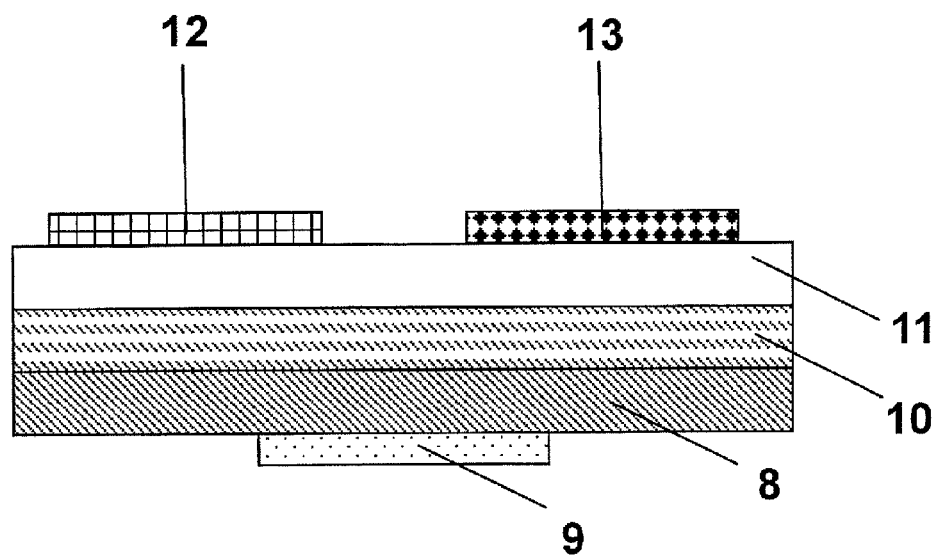
FIG. 3 illustrates a schematic sectional view illustrating another example of the structure of the organic TFT device.

FIG. 2 and FIG. 3 are sectional views illustrating examples of the structure of the organic TFT device. Reference numeral 8 represents the substrate, reference numeral 9 represents the gate electrode, reference numeral 10 represents the insulating layer, reference numeral 11 represents the organic semiconductor layer, reference numeral 12 represents the source electrode, and reference numeral 13 represents the drain electrode.

—Substrate—

The substrate is not particularly limited and can be of, for example, any one of the conventionally known constructions. Examples of the substrate include a glass (such as quartz glass), silicon, ceramic, and a plastic. Examples of the plastic include general-purpose resin substrates such as a polyethylene terephthalate, a polyethylene naphthalate, and a polycarbonate. A gas barrier film for reducing permeability for a gas such as oxygen or water vapor is preferably laminated on any such resin substrate.

—Gate Electrode—

The gate electrode is not particularly limited and can be of, for example, any one of the conventionally known constructions. As a material for the gate electrode, there may be used, for example: metals such as gold, platinum, chromium, tungsten, tantalum, nickel, copper, aluminum, silver, magnesium, and calcium or alloys thereof; and a polysilicon, amorphous silicon, graphite, ITO, zinc oxide, and a conductive polymer.

—Gate Insulating Layer—

The gate insulating layer is not particularly limited and can be of, for example, any one of the conventionally known constructions. As a material for the gate insulating layer, there may be used, for example: $SiO_2$, $Si_3N_4$, $SiON$, $Al_2O_3$, $Ta_2O_5$, amorphous silicon, a polyimide resin, a polyvinylphenol resin, a polyparaxylylene resin, a polymethyl methacrylate resin, and fluororesins (e.g., PTFE, PFA, PETFE, PCTFE, and CYTOP (trademark)).

—Organic Semiconductor Layer—

The organic semiconductor layer has only to contain the compound of the present invention and is not particularly limited. For example, the layer may be a layer formed substantially only of the compound of the present invention, or may contain any substance other than the compound of the present invention.

—Source Electrode and Drain Electrode—

Both the source electrode and the drain electrode are not particularly limited and can each be of, for example, any one of the conventionally known constructions. For each of the source electrode and the drain electrode, there may be used materials such as: metals, e.g., gold, platinum, chromium, tungsten, tantalum, nickel, copper, aluminum, silver, magnesium, and calcium or alloys thereof; and a polysilicon, amorphous silicon, graphite, ITO, zinc oxide, and a conductive polymer.

The construction of the lamination in the organic TFT device may be any one of a construction (i) having, from a substrate side, the gate electrode, the gate insulating layer, the organic semiconductor layer, and the source electrode and the drain electrode in the stated order, and a construction (ii) having, from the substrate side, the gate electrode, the gate insulating layer, the source electrode and the drain electrode, and the organic semiconductor layer in the stated order. Although a method of producing the organic TFT device is not particularly limited, in the case of the construction (i), the method is, for example, a top contact method involving sequentially laminating, on the substrate, the gate electrode, the gate insulating layer, the organic semiconductor layer, and the drain electrode and the source electrode. In the case of the construction (ii), the method is, for example, a bottom contact method involving sequentially laminating, on the substrate, the gate electrode, the gate insulating layer, the drain electrode and the source electrode, and the organic semiconductor layer.

Although a method of forming each of the gate electrode, the gate insulating layer, the source electrode, and the drain electrode is not particularly limited, each of the electrodes and the layer can be formed by a well-known film production method such as a vacuum deposition method, an electron beam deposition method, an RF sputtering method, a spin coating method, or a printing method with, for example, the foregoing material. Although a method of forming the organic semiconductor layer is not particularly limited, the layer can be formed by a well-known film production method such as the vacuum deposition method, the spin coating method, an inkjet method, or the printing method with, for example, the compound or organic semiconductor material of the present invention.

Although the applications of the organic TFT device are not particularly limited, the device is suitably used as, for example, a TFT device for driving a flexible display using a plastic substrate. In general, it is difficult to produce a TFT device constituted of an inorganic substance on the plastic substrate from a process viewpoint. However, in the step of producing the organic electronic device of the present invention formed of the organic TFT device, as described above, a process such as the vacuum deposition method, the spin coating method, the inkjet method, or the printing method is employed and no high-temperature process is employed, and hence a TFT device for driving a pixel can be formed on the plastic substrate. In particular, the compound of the present invention is soluble in a general-purpose organic solvent such as chloroform, tetrahydrofuran, or toluene. Accordingly, the compound enables the application of a low-cost process such as the spin coating method, the inkjet method, or the printing method, and is hence suitable for the production of an inexpensive, paper-like (flexible) display.

Another preferred embodiment of the organic electronic device containing the compound of the present invention is a photovoltaic device, preferably an organic thin-film solar cell. Specifically, the organic electronic device is a photovoltaic device having, on a substrate, a positive electrode, an organic semiconductor layer, and a negative electrode, in which the organic semiconductor layer contains the compound of the present invention.

The structure of the photovoltaic device of the present invention is described with reference to the drawings but the structure of the photovoltaic device of the present invention is by no means limited to those illustrated in the drawings.

Figure 4:
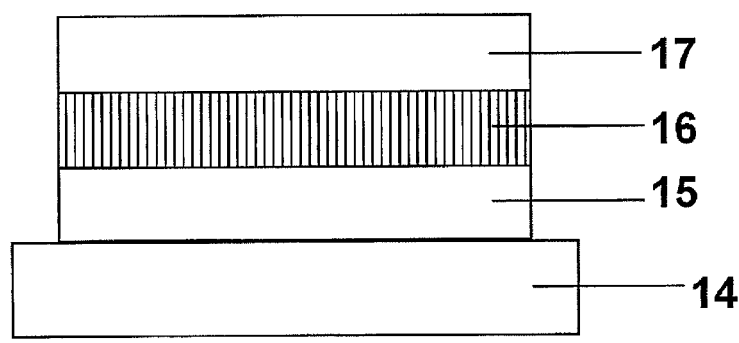
FIG. 4 is a schematic sectional view illustrating an example of the structure of a photovoltaic device.
Figure 5:
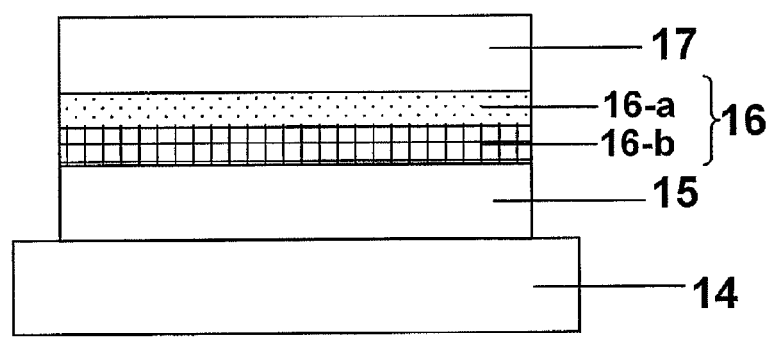
FIG. 5 is a schematic sectional view illustrating another example of the structure of the photovoltaic device.

FIG. 4 is a sectional view illustrating an example of the structure of a general photovoltaic device to be used in the present invention. Reference numeral 14 represents the substrate, reference numeral 15 represents the positive electrode, reference numeral 16 represents the organic semiconductor layer, and reference numeral 17 represents the negative electrode. In addition, FIG. 5 is a sectional view illustrating a structure example in the case where organic semiconductor layers are laminated. Reference symbol 16-$a$ represents an electron-donating organic semiconductor layer and reference symbol 16-$b$ represents an electron-accepting organic semiconductor layer.

—Substrate—

The substrate is not particularly limited and can be of, for example, any one of the conventionally known constructions. A glass substrate or transparent resin film having mechanical and thermal strengths, and having transparency is preferably used. Examples of the transparent resin film include a polyethylene, an ethylene-vinyl acetate copolymer, an ethylene-vinyl alcohol copolymer, a polypropylene, a polystyrene, a polymethyl methacrylate, a polyvinyl chloride, a polyvinyl alcohol, a polyvinyl butyral, nylon, a polyether ether ketone, a polysulfone, a polyether sulfone, a tetrafluoroethylene-perfluoroalkyl vinyl ether copolymer, a polyvinyl fluoride, a tetrafluoroethylene-ethylene copolymer, a tetrafluoroethylene-hexafluoropropylene copolymer, a polychlorotrifluoroethylene, a polyvinylidene fluoride, a polyester, a polycarbonate, a polyurethane, a polyimide, a polyether imide, a polyimide, and a polypropylene.

—Electrodes—

A conductive material having a large work function is preferably used as an electrode material for one electrode, and a conductive material having a small work function is preferably used as an electrode material for the other electrode. The electrode using the conductive material having a large work function serves as the positive electrode. In addition to metals such as gold, platinum, chromium, and nickel, metal oxides of, for example, indium and tin, and composite metal oxides thereof (such as an indium tin oxide (ITO) and an indium zinc oxide (IZO)) each having transparency are each preferably used as the conductive material having a large work function. Here, the conductive material to be used in the positive electrode is preferably capable of ohmic junction with the organic semiconductor layer. Further, when a hole-transporting layer to be described later is used, the conductive material to be used in the positive electrode is preferably capable of ohmic junction with the hole-transporting layer.

The electrode using the conductive material having a small work function serves as the negative electrode. Alkali metals and alkaline earth metals, specifically lithium, magnesium, and calcium are each used as the conductive material having a small work function. In addition, tin, silver, and aluminum are each preferably used. Further, alloys formed of the metals and electrodes formed of laminates of the metals are each preferably used. In addition, the introduction of a metal fluoride such as lithium fluoride or cesium fluoride into an interface between the negative electrode and an electron-transporting layer can increase an extracted current. Here, the conductive material to be used in the negative electrode is preferably capable of ohmic junction with the organic semiconductor layer. Further, when the electron-transporting layer to be described later is used, the conductive material to be used in the negative electrode is preferably capable of ohmic junction with the electron-transporting layer.

—Organic Semiconductor Layer—

The organic semiconductor layer contains the compound of the present invention. That is, the layer contains an electron-donating organic material containing the compound of the present invention and an electron-accepting organic material. Those materials are preferably mixed, and the electron-donating organic material and the electron-accepting organic material are preferably compatible with each other, or preferably undergo phase separation, at a molecular level. The domain size of the phase-separated structure, which is not particularly limited, is typically a size of 1 nm or more and 50 nm or less. In addition, when the electron-donating organic material and the electron-accepting organic material are laminated, it is preferred that a layer having the electron-donating organic material showing a p-type semiconductor characteristic be on a positive electrode side and a layer having the electron-accepting organic material showing an n-type semiconductor characteristic be on a negative electrode side. The organic semiconductor layer has a thickness of preferably 5 nm to 500 nm, more preferably 30 nm to 300 nm. When the layers are laminated, the layer having the electron-donating organic material of the present invention has a thickness of preferably 1 nm to 400 nm, more preferably 15 nm to 150 nm out of the thickness.

The electron-donating organic material may be formed only of the compound of the present invention represented by the general formula (1), or may contain any other electron-donating organic material. Examples of the other electron-donating organic material include: conjugated polymers such as a polythiophene-based polymer, a benzothiadiazole-thiophene-based derivative, a benzothiadiazole-thiophene-based copolymer, a poly-p-phenylenevinylene-based polymer, a poly-p-phenylene-based polymer, a polyfluorene-based polymer, a polypyrrole-based polymer, a polyaniline-based polymer, a polyacetylene-based polymer, and a polythienylene vinylene-based polymer; and low-molecular weight organic compounds such as phthalocyanine derivatives including H2 phthalocyanine (H2Pc), copper phthalocyanine (CuPc), and zinc phthalocyanine (ZnPc), porphyrin derivatives, triarylamine derivatives including N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives including 4,4'-di(carbazol-9-yl)biphenyl (CBP), and oligothiophene derivatives (e.g., terthiophene, quaterthiophene, sexithiophene, and octithiophene).

Materials for the photovoltaic device of the present invention preferably further contain the electron-accepting organic material (n-type organic semiconductor) because the compound of the present invention represented by the general formula (1) shows electron-donating property (p-type semiconductor characteristic). The combination of the compound of the present invention and the electron-accepting organic material can additionally improve the photoelectric conversion efficiency of the photovoltaic device.

The electron-accepting organic material to be used for the photovoltaic device of the present invention is an organic material showing an n-type semiconductor characteristic. Examples thereof include: 1,4,5,8-naphthalenetetracarboxylic dianhydride (NTCDA); 3,4,9,10-perylenetetracarboxylic dianhydride (PTCDA); 3,4,9,10-perylenetetracarboxylic bis-benzimidazole (PTCBI); N,N'-dioctyl-3,4,9,10-naphthyltetracarboxy diimide (PTCDI-C8H); oxazole derivatives such as 2-(4-biphenylyl)-5-(4-t-butylphenyl)-1,3,4-oxadiazole (PBD) and 2,5-di(1-naphthyl)-1,3,4-oxadiazole (BND); triazole derivatives such as 3-(4-biphenylyl)-4-phenyl-5-(4-t-butylphenyl)-1,2,4-triazole (TAZ); phenanthroline derivatives; phosphine oxide derivatives; fullerene compounds (e.g., non-substituted fullerene compounds exemplified by C60, C70, C76, C78, C82, C84, C90, and C94, [6,6]-phenyl-C61-butyric acid methyl ester ([6,6]-PCBM), [5,6]-phenyl-C61-butyric acid methyl ester ([5,6]-PCBM), [6,6]-phenyl-C61-butyric acid hexyl ester ([6,6]-PCBH), [6,6]-phenyl-C6'-butyric acid dodecyl ester ([6,6]-PCBD), phenyl-C71-butyric acid methyl ester (PC70BM), and phenyl-C85-butyric acid methyl ester (PC84BM)); carbon nanotubes (CNT's); and derivatives each obtained by introducing a cyano group to a poly-p-phenylenevinylene-based polymer (CN-PPV's). Of those, fullerene compounds are preferably used because of their high charge separation rates and high electron transfer rates.

In the photovoltaic device of the present invention, the hole-transporting layer may be provided between the positive electrode and the organic semiconductor layer. A conductive polymer such as a polythiophene-based polymer, a poly-p-phenylenevinylene-based copolymer, or a polyfluorene-based polymer, or a low-molecular weight organic compound showing a p-type semiconductor characteristic such as a phthalocyanine derivative (e.g., H2Pc, CuPc, or ZnPc) or a porphyrin derivative is preferably used as a material for forming the hole-transporting layer. In particular, a polyethylenedioxythiophene (PEDOT) that is a polythiophene-based polymer or a product obtained by adding a polystyrene sulfonate (PSS) to the PEDOT is preferably used. The hole-transporting layer has a thickness of preferably 5 nm to 600 nm, more preferably 30 nm to 200 nm.

In addition, in the photovoltaic device of the present invention, the electron-transporting layer may be provided between the organic semiconductor layer and the negative electrode. Although a material for forming the electron-transporting layer is not particularly limited, organic materials showing n-type semiconductor characteristics like the electron-accepting organic materials (such as NTCDA, PTCDA, PTCDI-C8H, the oxazole derivatives, the triazole derivatives, the phenanthroline derivatives, the phosphine oxide derivatives, the fullerene compounds, the CNT's, and the CN-PPV's) are each preferably used. The electron-transporting layer has a thickness of preferably 5 nm to 600 nm, more preferably 30 nm to 200 nm.

In addition, in the photovoltaic device of the present invention, two or more organic semiconductor layers may be laminated (put in tandem) through one or more intermediate electrodes to form series junction. For example, a laminate construction "substrate/positive electrode/first organic semiconductor layer/intermediate electrode/second organic semiconductor layer/negative electrode" can be given. Such lamination can increase an open-circuit voltage. It should be noted that the hole-transporting layer may be provided between the positive electrode and the first organic semiconductor layer, and between the intermediate electrode and the second organic semiconductor layer, or the hole-transporting layer may be provided between the first organic semiconductor layer and the intermediate electrode, and between the second organic semiconductor layer and the negative electrode.

In the case of such laminate construction, it is preferred that at least one layer of the organic semiconductor layers contain the compound of the present invention represented by the general formula (1) and the other layer contain an electron-donating organic material having a band gap different from that of the electron-donating organic material of the present invention for preventing a reduction in short-circuit current. Examples of such electron-donating organic material include the above-mentioned materials, that is: the conjugated polymers such as the polythiophene-based polymer, the poly-p-phenylenevinylene-based polymer, the poly-p-phenylene-based polymer, the polyfluorene-based polymer, the polypyrrole-based polymer, the polyaniline-based polymer, the polyacetylene-based polymer, and the polythienylene vinylene-based polymer; and the low-molecular weight organic compounds such as the phthalocyanine derivatives including H2 phthalocyanine (H2Pc), copper phthalocyanine (CuPc), and zinc phthalocyanine (ZnPc), the porphyrin derivatives, the triarylamine derivatives including N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), the carbazole derivatives including 4,4'-di(carbazol-9-yl)biphenyl (CBP), and the oligothiophene derivatives (e.g., terthiophene, quaterthiophene, sexithiophene, and octithiophene).

In addition, as a material for the intermediate electrode as used herein, a material having high conductivity is preferred. Examples thereof include the above-mentioned materials, that is: the metals such as gold, platinum, chromium, nickel, lithium, magnesium, calcium, tin, silver, and aluminum; the metal oxides of, for example, indium and tin, and complex metal oxides thereof (e.g., indium tin oxide (ITO) and indium zinc oxide (IZO)) each having transparency; the alloys formed of the metals; the laminates of the metals; the polyethylenedioxythiophene (PEDOT); and the product obtained by adding a polystyrene sulfonate (PSS) to the PEDOT. Although the intermediate electrode preferably has light permeability, sufficient light permeability can be secured by reducing its thickness in many cases even when the electrode is made of a material like a metal having low light permeability.

Any one of the methods such as spin coating application, blade coating application, slit die coating application, screen printing application, bar coater application, cast application, a printing transfer method, a dip-pulling method, an inkjet method, a spray method, and a vacuum deposition method may be employed for the formation of the organic semiconductor layer, and a formation method has only to be selected in accordance with organic semiconductor layer characteristics to be obtained such as thickness control and orientation control.

The compound of the present invention or the organic semiconductor material of the present invention containing the compound of the present invention has a high charge mobility, solvent solubility, oxidation stability, and good film formability, and an organic semiconductor device using the compound or the material also exerts high characteristics. An organic field-effect transistor and an organic thin-film solar cell can be given as specific examples of the organic semiconductor device capable of taking advantage of the features of the organic semiconductor material of the present invention. Further, the incorporation of those organic semiconductor devices enables the devices to find applications in displays such as an organic EL panel and electronic paper, liquid crystal displays, information tags, and large-area sensors such as an electronic artificial skin sheet and a sheet-type scanner.

EXAMPLES

Hereinafter, the present invention is described in more detail with reference to examples. It should be appreciated that the present invention is not limited to these examples and may be carried out in various forms as long as the various forms do not deviate from the gist of the present invention.

The routes described below were used to synthesize chalcogen-containing aromatic compounds used in the present invention. It should be noted that the number of each compound corresponds to the number given to each chemical formula described above.

Example 1

Synthesis of Compound 1-1

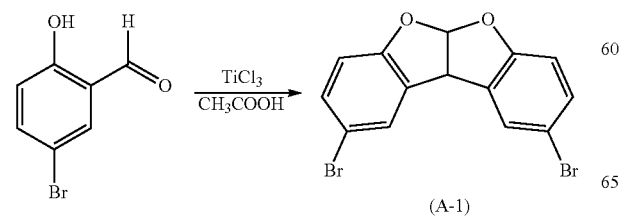

Under a nitrogen atmosphere, 50.0 g (0.25 mol) of 5-bromosalicylaldehyde and 400 ml of acetic acid were loaded, and were then stirred at 80° C. 293.0 Grams (0.38 mol) of titanium trichloride were dropped to the mixture and then the whole was stirred for 5 hours. After that, the reaction solution was cooled to room temperature. 500 Milliliters of ethyl acetate were added to the reaction solution and then an organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 16.5 g (0.045 mol, 36% yield) of an intermediate A-1.

Under a nitrogen atmosphere, 6.8 g (0.018 mol) of the intermediate A-1, 4.86 g (0.027 mol) of N-bromosuccinimide, 0.26 g (0.001 mol) of benzoyl peroxide, and 900 ml of carbon tetrachloride were loaded, and were then stirred at 80° C. for 24 hours. After that, the mixture was cooled to room temperature and then inorganic salt was separated by filtration. 100 Milliliters of methylene chloride were added to the remainder and then an organic layer was washed with an aqueous solution of sodium thiosulfate (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 7.6 g (0.017 mol, 92% yield) of an intermediate A-2.

-continued

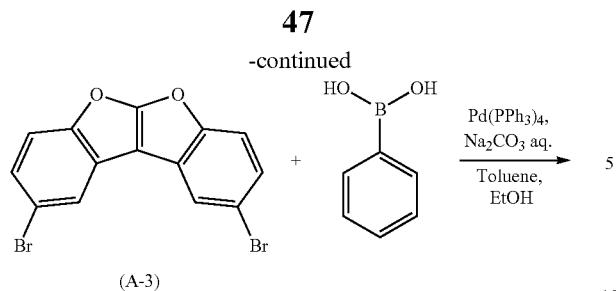

(A-3)

Example 2

Synthesis of Compound 1-7

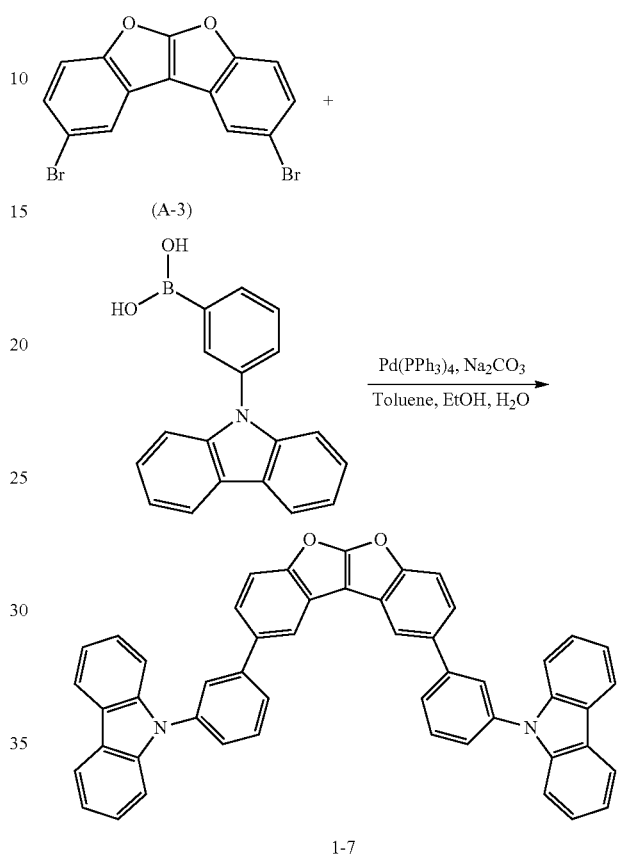

Under a nitrogen atmosphere, 6.0 g (0.013 mol) of the intermediate A-2, 100 ml of triethylamine, and 1,200 ml of ethanol were loaded, and were then stirred at 100° C. for 15 days. After that, the mixture was cooled to room temperature and then the solvent was distilled off under reduced pressure. The resultant residue was purified by column chromatography to provide 4.1 g (0.011 mol, 84% yield) of an intermediate A-3.

Under a nitrogen atmosphere, 5.0 g (0.014 mol) of the intermediate A-3, 10.0 g (0.082 mol) of phenylboronic acid, 1.0 g (0.0082 mol) of tetrakis(triphenylphosphine)palladium [0], 200 ml of toluene, and 100 ml of ethanol were loaded, and were then stirred. An aqueous solution of sodium carbonate prepared by dissolving 30.5 g (0.33 mol) of sodium carbonate in 200 ml of water was added to the mixture, and then the whole was stirred at 100° C. for 5 hours. The reaction solution was cooled to room temperature. An organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 4.1 g (0.011 mol, 81% yield) of a compound 1-1 as a white powder.

Figure 6:
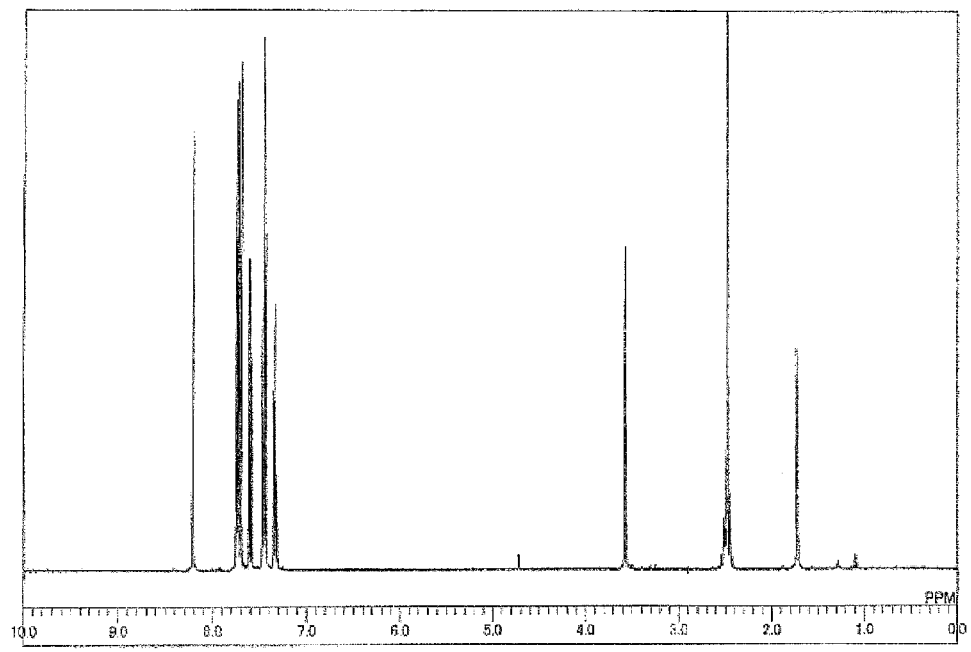
FIG. 6 shows the $^1$H-NMR chart of a compound 1-1.

The APCI-TOFMS of the compound showed an [M+H]$^+$ peak at an m/z of 361. FIG. 6 shows the results of the $^1$H-NMR measurement of the compound (measurement solvent: THF-d8).

3.6 Grams (0.0052 mol, 79% yield) of a compound 1-7 as a white solid were obtained in the same manner as in the synthesis of the compound 1-1 except that carbazolyl-3-phenylboronic acid was used instead of phenylboronic acid.

Figure 7:
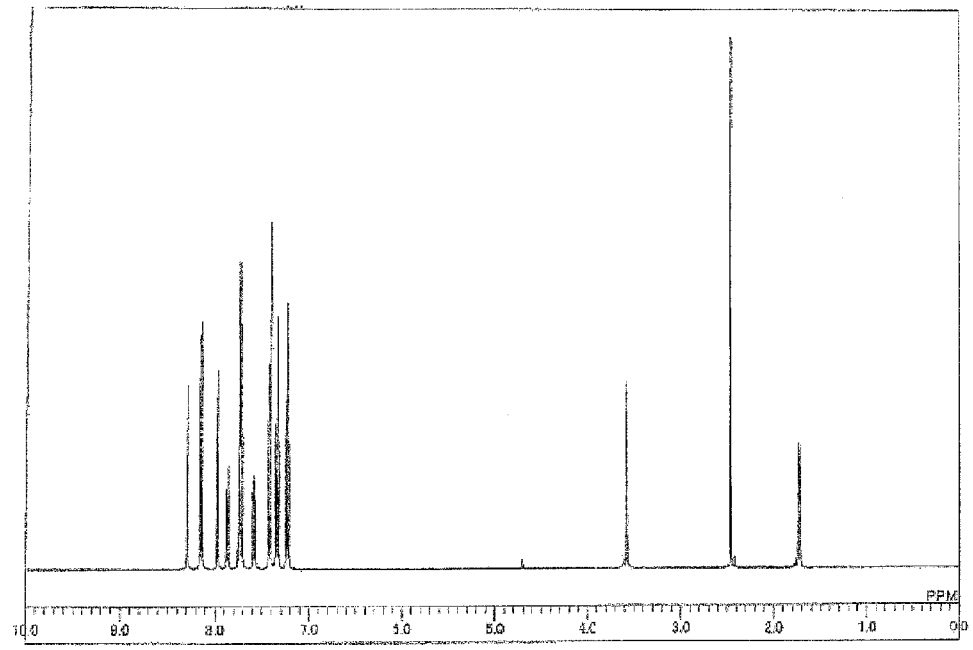
FIG. 7 shows the $^1$H-NMR chart of a compound 1-7.

The APCI-TOFMS of the compound showed an [M+H]$^+$ peak at an m/z of 691. FIG. 7 shows the results of the $^1$H-NMR measurement of the compound (measurement solvent: THF-d8).

Example 3

Synthesis of Compound 1-9

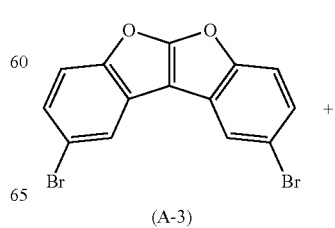

(A-3)

49

-continued

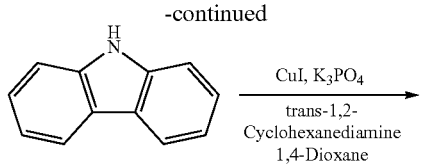

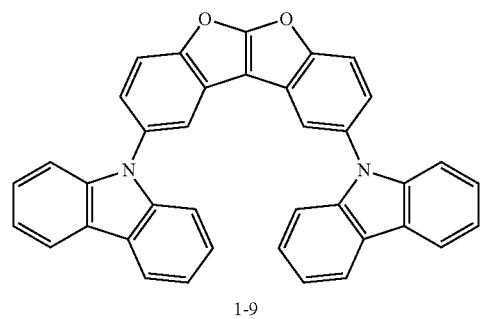

1-9

Under a nitrogen atmosphere, 4.5 g (0.012 mol) of the intermediate A-3, 12.0 g (0.072 mol) of carbazole, 1.4 g (0.0072 mol) of copper iodide, 61.1 g (0.29 mol) of tripotassium phosphate, and 450 ml of 1,4-dioxane were loaded, and were then stirred. 6.6 Grams (0.058 mol) of trans-1,2-cyclohexanediamine were added to the mixture and then the whole was stirred at 120° C. for 48 hours. Next, the reaction solution was cooled to room temperature and then inorganic salt was separated by filtration. After that, the solvent was distilled off under reduced pressure. The resultant residue was purified by column chromatography to provide 5.2 g (0.0096 mol, 80% yield) of a compound 1-9 as a white solid.

Figure 8:
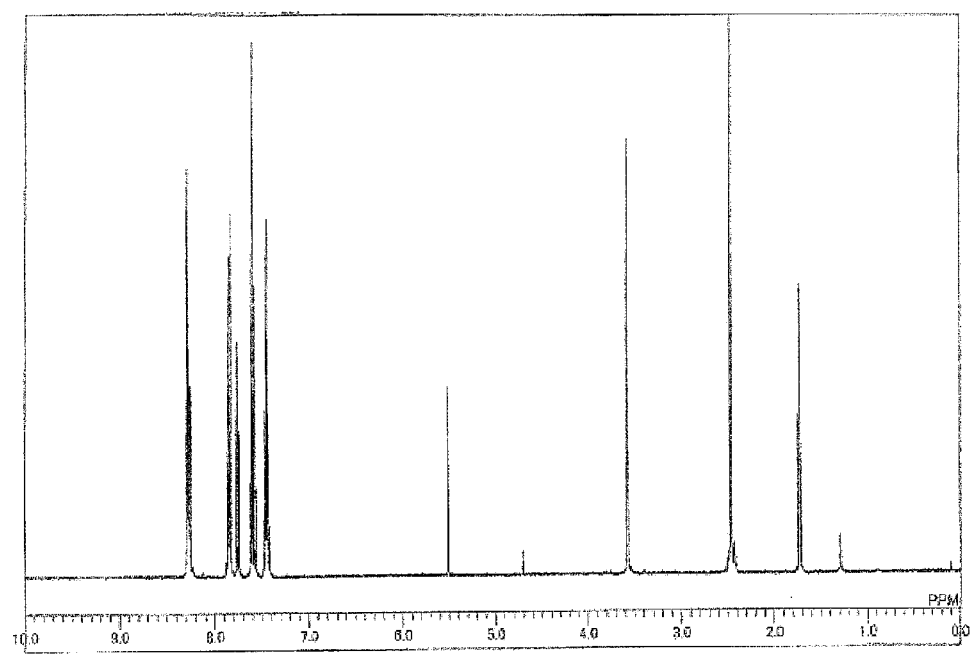
FIG. 8 shows the $^1$H-NMR chart of a compound 1-11.

The APCI-TOFMS of the compound showed an [M+H]$^+$ peak at an m/z of 539. FIG. 8 shows the results of the $^1$H-NMR measurement of the compound (measurement solvent: THF-d8).

50

Example 4

Synthesis of Compound 1-11

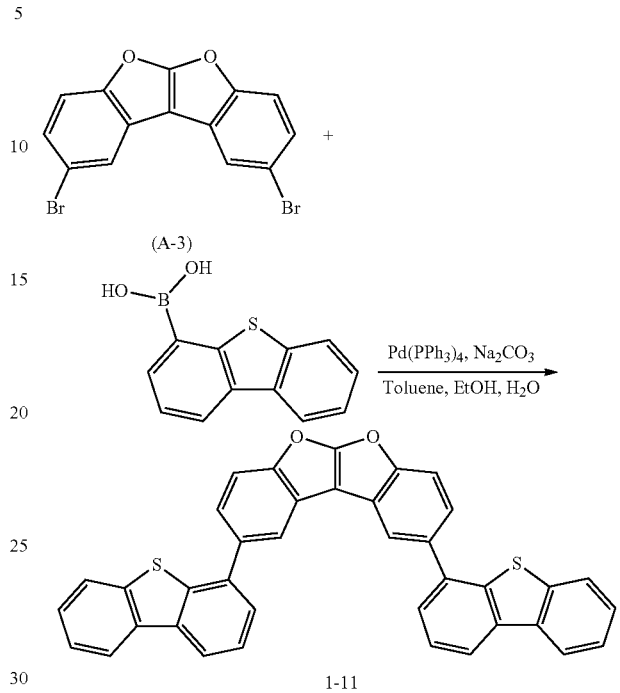

2.9 Grams (0.0051 mol, 73% yield) of a compound 1-11 as a white solid were obtained in the same manner as in the synthesis of the compound 1-1 except that 4-dibenzothiopheneboronic acid was used instead of phenylboronic acid.

The APCI-TOFMS of the compound showed an [M+H]$^+$ peak at an m/z of 573. FIG. 9 shows the results of the $^1$H-NMR measurement of the compound (measurement solvent: THF-d8).

Example 5

Synthesis of Compound 1-25

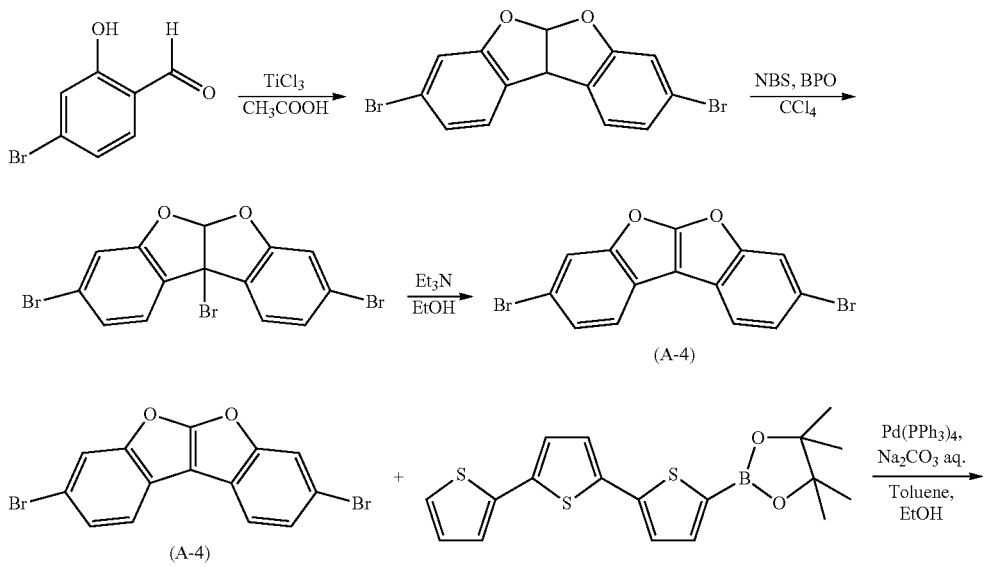

-continued

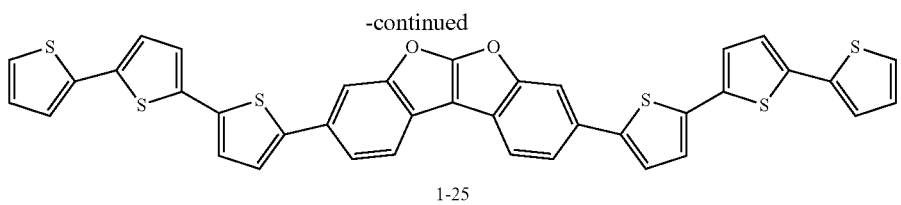

1-25

An intermediate A-4 was obtained in the same manner as in the synthesis of the intermediate A-3 except that 4-bromosalicylaldehyde was used instead of 5-bromosalicylaldehyde.

1.3 Grams (0.0018 mol, 72% yield) of a compound 1-25 as a white solid were obtained in the same manner as in the synthesis of the compound 1-1 except that the intermediate A-4 was used instead of the intermediate A-3 and 2,2':5',2"-terthiophene-5-boronic acid pinacol ester was used instead of phenylboronic acid.

The APCI-TOFMS of the compound showed an [M+H]+ peak at an m/z of 701.

Example 6

Synthesis of Compound 2-16

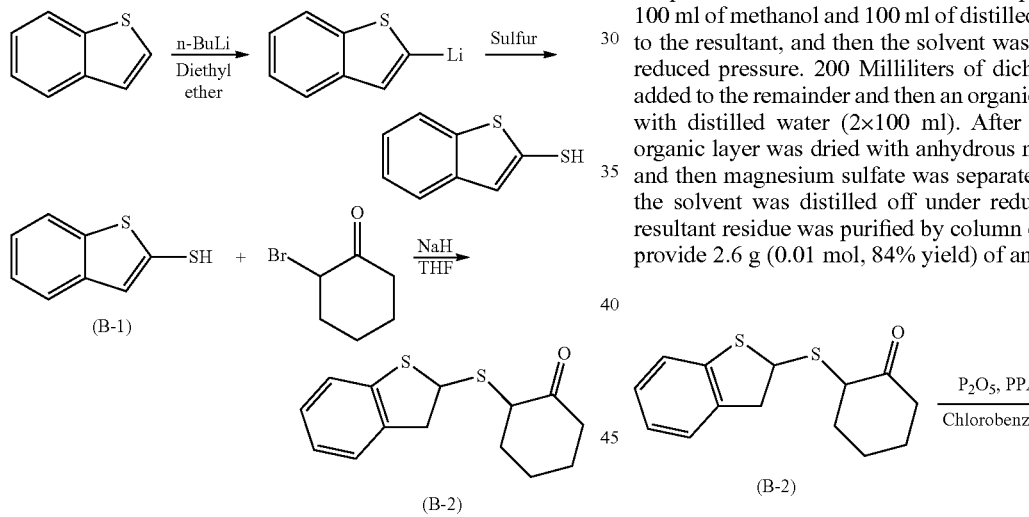

Under a nitrogen atmosphere, 10.0 g (0.075 mol) of benzo[b]thiophene and diethyl ether were loaded, and were then stirred at 0° C. 51 Milliliters (0.082 mol) of 1.60-M n-butyllithium were dropped to the mixture and then the whole was stirred for 1 hour. After that, 2.6 g (0.082 mol) of sulfur were added to the resultant at 0° C. and then the mixture was stirred at room temperature for 6 hours. The reaction liquid was poured into ice water and then hydrochloric acid was used to adjust the pH of the mixture to 1, followed by the addition of 200 ml of diethyl ether. An organic layer was washed with distilled water (2×100 ml). After that, the resultant organic layer was dried with anhydrous magnesium sulfate, and then magnesium sulfate was separated by filtration and the solvent was distilled off under reduced pressure. 100 Milliliters of tetrahydrofuran (THF) were added to the remainder, and then sodium borohydride was added to the mixture while the mixture was stirred at 0° C., followed by stirring at room temperature for 2 hours. The reaction liquid was poured into ice water and then hydrochloric acid was used to adjust the pH of the mixture to 1, followed by the addition of 200 ml of diethyl ether. An organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 11.2 g (0.067 mol, 89% yield) of an intermediate B-1.

Under a nitrogen atmosphere, 0.5 g (0.014 mol) of 62.0% sodium hydride and 100 ml of THF were loaded, and were then stirred at 0° C. 2.0 Grams (0.012 mol) of the intermediate B-1 dissolved in 50 ml of THF were dropped to the mixture and then the whole was stirred for 1 hour while its temperature was kept at 0°. 2.5 Grams (0.014 mol) of 2-bromocyclohexanone dissolved in 50 ml of THF were dropped to the mixture and then the whole was stirred for 2 hours while its temperature was increased to room temperature. After that, 100 ml of methanol and 100 ml of distilled water were added to the resultant, and then the solvent was distilled off under reduced pressure. 200 Milliliters of dichloromethane were added to the remainder and then an organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 2.6 g (0.01 mol, 84% yield) of an intermediate B-2.

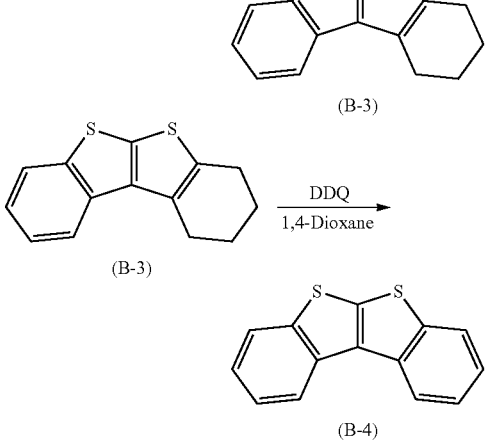

Under a nitrogen atmosphere, 3.2 g (0.011 mol) of diphosphorus pentoxide, 1.0 g of a polyphosphoric acid, and 100 ml of chlorobenzene were loaded, and were then stirred at room temperature. 3.0 Grams (0.011 mol) of the intermediate B-2 dissolved in 50 ml of chlorobenzene were dropped to the mixture and then the whole was stirred at 170° C. for 18 hours. After the completion of the reaction, the resultant was cooled to room temperature and then the solvent was distilled off under reduced pressure. Next, 100 ml of chloroform were added to the remainder and then an organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 1.9 g (0.0077 mol, 70% yield) of an intermediate B-3.

Under a nitrogen atmosphere, 4.6 g (0.020 mol) of 2,3-dichloro-5,6-dicyano-1,4-benzoquinone and 100 ml of 1,4-dioxane were loaded, and were then stirred at 120° C. 5.0 Grams (0.020 mol) of an intermediate G dissolved in 100 ml of 1,4-dioxane were dropped to the mixture and then the whole was stirred for 50 hours. Next, the reaction solution was cooled to room temperature and then inorganic salt was separated by filtration. After that, the solvent was distilled off under reduced pressure. 200 Milliliters of dichloromethane were added to the remainder and then an organic layer was washed with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 3.0 g (0.012 mol, 62% yield) of an intermediate B-4.

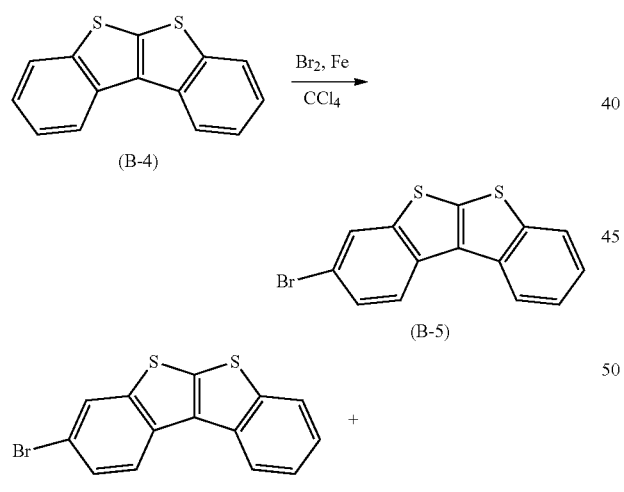

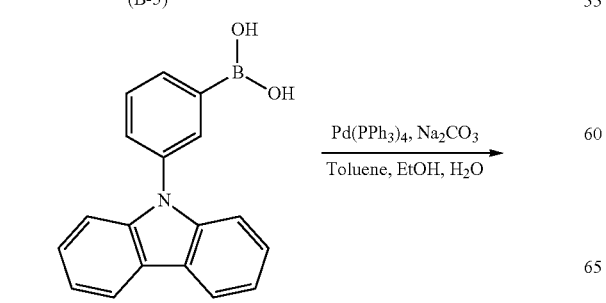

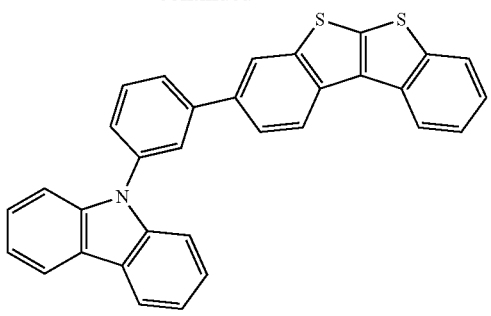

2-16

4.0 Grams (0.017 mol) of the intermediate B-4, 0.1 g (0.002 mol) of an iron powder, and 100 ml of carbon tetrachloride were loaded, and were then stirred at 0° C. 1.3 Grams (0.017 mol) of bromine were slowly dropped to the mixture. After that, the resultant was stirred at room temperature for 12 hours and was then cooled to 0° C., followed by the addition of an aqueous solution of sodium sulfite. An organic layer was washed with an aqueous solution of sodium thiosulfate (3×100 ml). After that, the resultant organic layer was dried with anhydrous magnesium sulfate, and then magnesium sulfate was separated by filtration and the solvent was distilled off under reduced pressure. The resultant residue was purified by column chromatography to provide 2.1 g (0.006 mol, 38% yield) of an intermediate B-5.

1.5 Grams (0.003 mol, 66% yield) of a compound 2-16 as a white solid were obtained in the same manner as in the synthesis of the compound 1-1 except that the intermediate B-5 was used instead of the intermediate A-3 and carbazolyl-3-phenylboronic acid was used instead of phenylboronic acid.

Example 7

Synthesis of Compound 2-18

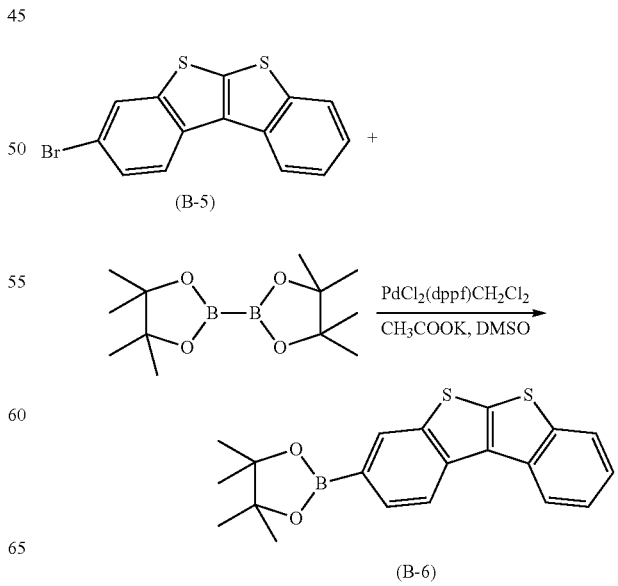

55

-continued

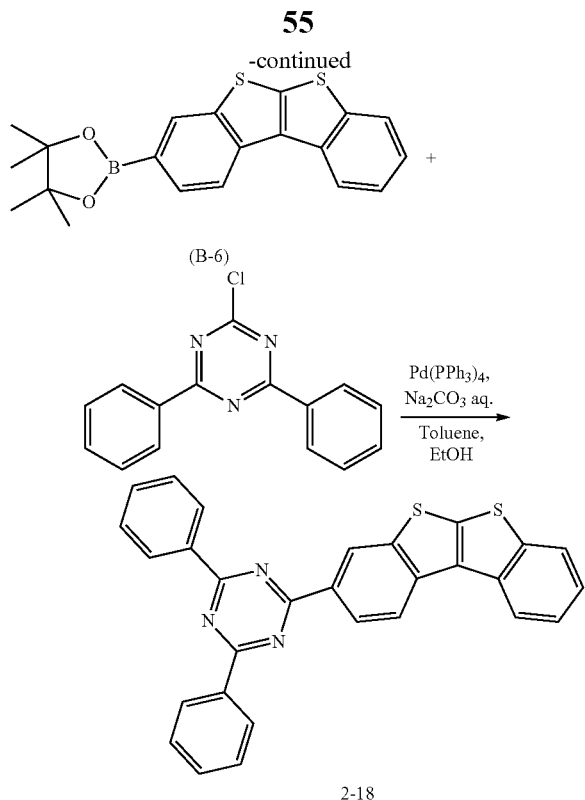

Under a nitrogen atmosphere, 2.0 g (0.006 mol) of the intermediate B-5, 1.8 g (0.007 mol) of bis(pinacolato)diboron, 1.8 g (0.018 mol) of potassium acetate, and 100 ml of dimethyl sulfoxide (DMSO) were loaded, and were then stirred at 60° C. 0.15 Gram (0.0002 mol) of a [1,1'-bis(biphenylphosphino)-ferrocene]dichloride dichloropalladium complex was added to the mixture and then the whole was stirred at 80° C. for 4 hours. The resultant reaction solution was dropped to 200 ml of water and then the mixture was stirred for 1 hour. After that, a precipitated solid was separated by filtration and then the solid was dissolved in 200 ml of dichloromethane, followed by the washing of an organic layer with distilled water (2×100 ml). After that, the resultant organic layer was dried with anhydrous magnesium sulfate, and then magnesium sulfate was separated by filtration and the solvent was distilled off under reduced pressure. The resultant residue was purified by column chromatography to provide 1.6 g (0.004 mol, 68% yield) of an intermediate B-6.

3.2 Grams (0.0068 mol, 83% yield) of a compound 2-18 as a white solid were obtained in the same manner as in the synthesis of the compound 1-1 except that the intermediate B-6 was used instead of the intermediate A-3 and diphenylchlorotriazine was used instead of phenylboronic acid.

56

Example 8

Synthesis of Compound 2-20

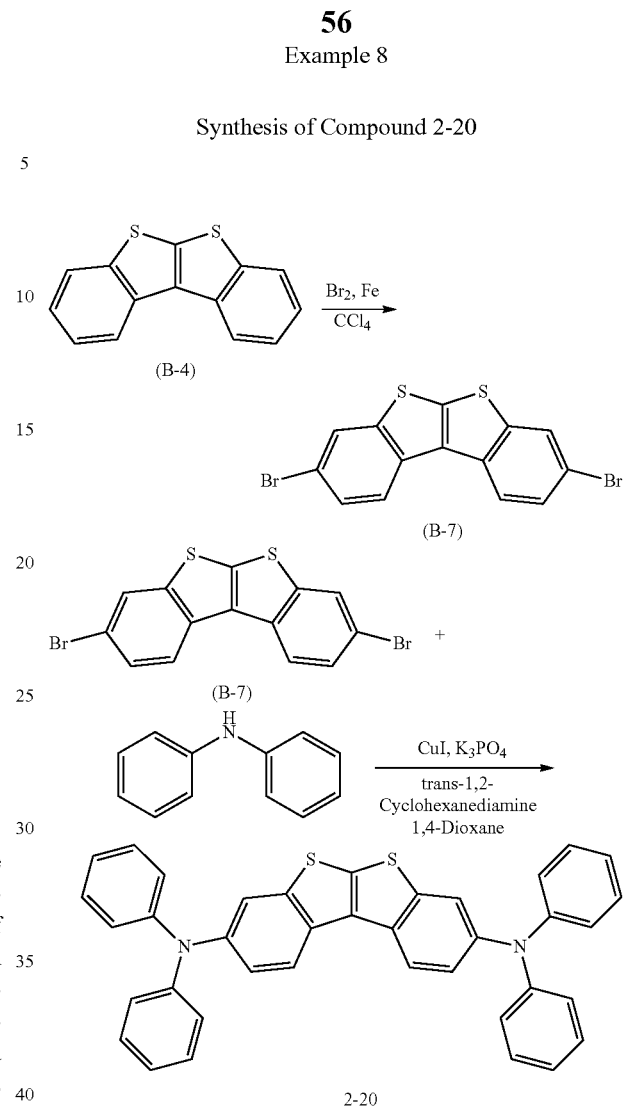

An intermediate B-7 was obtained in the same manner as in the synthesis of the intermediate B-5 except that the molar amount of bromine was set to be 2.2 times as large as that of the intermediate B-4.

4.9 Grams (0.0085 mol, 85% yield) of a compound 2-20 as a white solid were obtained in the same manner as in the synthesis of the compound 1-9 except that, under a nitrogen atmosphere, the intermediate B-7 was used instead of the intermediate A-3 and diphenylamine was used instead of carbazole.

Example 9

Synthesis of Compound 2-23

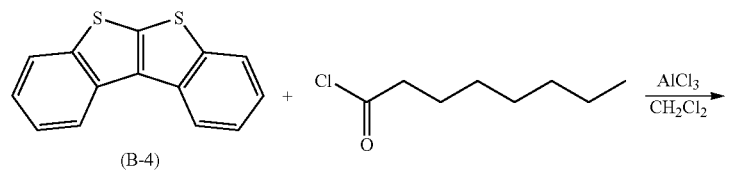

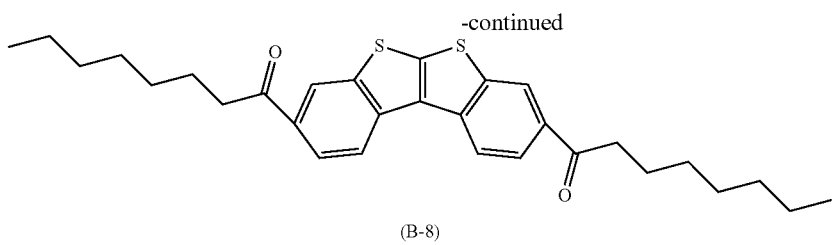

(B-8)

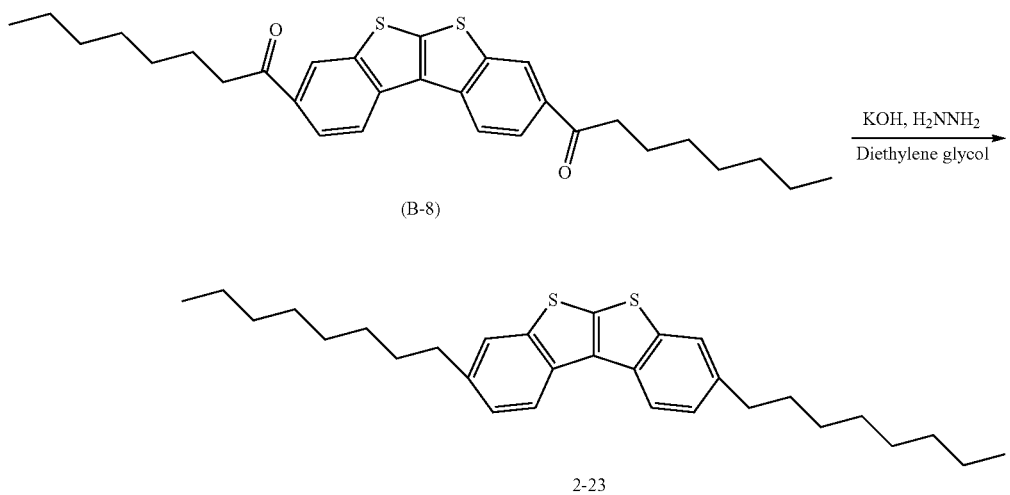

Under a nitrogen atmosphere, 2.0 g (0.0083 mol) of the intermediate B-4 and 200 ml of dichloromethane were loaded, and were then stirred at −10° C. 5.6 Grams (0.042 mol) of aluminum chloride were dropped to the mixture. After that, the reaction solution was cooled to −78° C. and then 6.8 g (0.042 mol) of n-octanoyl chloride were dropped to the solution. After that, the mixture was stirred for 60 hours while its temperature was kept at −78° C. After the completion of the reaction, the temperature of the resultant was increased to room temperature and then 50 ml of distilled water were added to the resultant. A precipitated solid was taken by filtration and then recrystallization was performed to provide 2.4 g (0.005 mol, 59% yield) of an intermediate B-8.

Under a nitrogen atmosphere, 3.0 g (0.006 mol) of the intermediate B-8, 1.7 g (0.03 mol) of potassium hydroxide, 4.9 g (0.15 mol) of hydrazine, and 300 ml of diethylene glycol were loaded, and were then heated at 210° C. for 6 hours. After the completion of the reaction, the resultant was cooled to room temperature and then a precipitated solid was separated by filtration. After that, the solid was purified by column chromatography to provide 1.6 g (0.0034 mol, 55% yield) of a compound 2-23 as a white powder.

Example 10

Synthesis of Compound 2-24

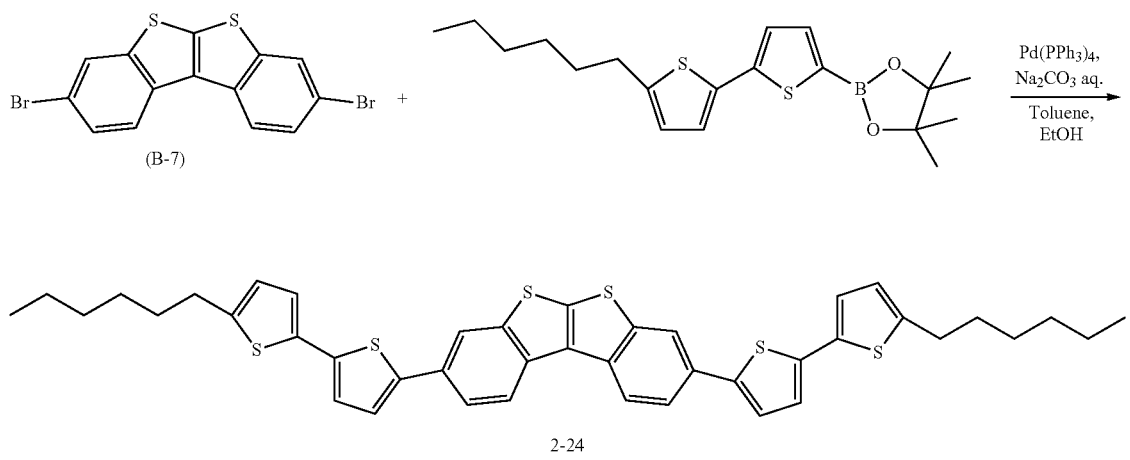

1.4 Grams (0.002 mol, 74% yield) of a compound 2-24 as a white solid were obtained in the same manner as in the synthesis of the compound 1-1 except that the intermediate B-7 was used instead of the intermediate A-3 and 5'-hexyl-2, 2'-bithiophene-5-boronic acid pinacol ester was used instead of phenylboronic acid.

Example 11

Each thin film was laminated by a vacuum deposition method at a degree of vacuum of $4.0 \times 10^{-5}$ Pa on a glass substrate on which an anode formed of an ITO having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 40 nm to serve as a hole-transporting layer. Next, the compound 1-1 as a host material and tris(2-phenylpyridine)iridium(III) (Ir(ppy)$_3$) as a phosphorescent light-emitting dopant were co-deposited from different deposition sources onto the hole-transporting layer to form a light-emitting layer having a thickness of 40 nm. The concentration of Ir(ppy)$_3$ in the light-emitting layer was 10.0 wt %. Next, tris(8-hydroxyquinolinato)aluminum(III) (Alq3) was formed into a layer having a thickness of 20 nm to serve as an electron-transporting layer. Further, lithium fluoride (LiF) was formed into a layer having a thickness of 1.0 nm on the electron-transporting layer to serve as an electron-injecting layer. Finally, aluminum (Al) was formed into a layer having a thickness of 70 nm on the electron-injecting layer to serve as an electrode. Thus, an organic EL device was produced.

An external power source was connected to the resultant organic EL device to apply a DC voltage to the device. As a result, the device was observed to have such light-emitting characteristics as shown in Table 1. The columns "luminance," "voltage," and "luminous efficiency" in Table 1 show values at 10 mA/cm$^2$. It should be noted that it was found that the local maximum wavelength of the emission spectrum of the device was 530 nm and hence light emission from Ir(ppy)$_3$ was obtained.

Example 12

An organic EL device was produced in the same manner as in Example 1 except that the compound 1-7 was used as the host material for the light-emitting layer.

Example 13

An organic EL device was produced in the same manner as in Example 1 except that the compound 1-9 was used as the host material for the light-emitting layer.

Example 14

An organic EL device was produced in the same manner as in Example 1 except that the compound 1-11 was used as the host material for the light-emitting layer.

Example 15

An organic EL device was produced in the same manner as in Example 1 except that the compound 1-25 was used as the host material for the light-emitting layer.

Example 16

An organic EL device was produced in the same manner as in Example 1 except that the compound 2-16 was used as the host material for the light-emitting layer.

Example 17

An organic EL device was produced in the same manner as in Example 1 except that the compound 2-18 was used as the host material for the light-emitting layer.

Example 18

An organic EL device was produced in the same manner as in Example 1 except that the compound 2-20 was used as the host material for the light-emitting layer.

The light-emitting characteristics of the organic EL devices produced in Examples 12 to 18 at 10 mA/cm$^2$ were measured in the same manner as in Example 11. It was found that the local maximum wavelength of the emission spectrum of each of the devices was 530 nm and hence light emission from Ir(ppy)$_3$ was obtained. Table 1 shows the light-emitting characteristics.

TABLE 1

| | | Light-emitting characteristic | | |
| --- | --- | --- | --- | --- |
| | Host compound | Luminance (cd/m$^2$) | Voltage (V) | Visual luminous efficiency (lm/W) |
| Example 11 | 1-1 | 2920 | 8.5 | 10.8 |
| 12 | 1-7 | 3660 | 8.4 | 13.7 |
| 13 | 1-9 | 3600 | 8.4 | 13.5 |
| 14 | 1-11 | 3410 | 8.1 | 13.2 |
| 15 | 1-25 | 3190 | 8.2 | 12.2 |
| 16 | 2-16 | 3630 | 8.3 | 13.7 |
| 17 | 2-18 | 3130 | 8.2 | 12.0 |
| 18 | 2-20 | 2980 | 8.5 | 11.0 |
| Comparative Example 1 | CBP | 2420 | 9.3 | 8.2 |

Example 21

An organic TFT device having a construction illustrated in FIG. 2 was produced and then the organic semiconductor material of the present invention was evaluated for its characteristics. First, a silicon wafer (n-doped) having a thermally grown silicon oxide layer having a thickness of about 300 nm was washed with a solution of sulfuric acid in hydrogen peroxide water and then boiled with isopropyl alcohol, followed by drying. The resultant silicon wafer was subjected to spin coating with a photoresist and then the photoresist was exposed with an exposing machine through a photomask. Next, the photoresist was subjected to development with a developer and then washed with ion-exchanged water, followed by air-drying. Chromium having a thickness of 3 nm was deposited by a vacuum deposition method onto the silicon wafer to which the patterned photoresist had been applied, and then gold having a thickness of 50 nm was deposited by the method onto chromium. A source electrode and a drain electrode were produced on the silicon wafer by immersing the silicon wafer in a remover solution. The silicon wafer on which the source electrode and the drain electrode had been produced was washed with acetone. Further, the washed product was boiled with isopropyl alcohol and then dried, followed by immersion in a solution of octyltrichlorosilane in toluene having a concentration of about $1 \times 10^{-6}$ M overnight. After that, the immersed product was washed with toluene and isopropyl alcohol, and was then heated at 110° C. for about 10 minutes. Thus, an organic field-effect transistor substrate subjected to an octyltrichlorosilane (OTS) treatment was produced. The substrate had a channel length L of 25 μm and a channel width W of 15.6 μm.

Next, a solution (1 wt %) of the compound 1-1 in chlorobenzene was filtered with a 0.2-μm syringe filter, and then the top of the substrate subjected to the OTS treatment was subjected to spin coating with the solution under the conditions of room temperature, 1,000 rpm, and 30 seconds. Next, the resultant was dried at 80° C. for 30 minutes. At this time, the thickness of an organic semiconductor layer was 50 nm. Thus, an organic field-effect transistor having the structure illustrated in FIG. 2 was obtained.

A voltage of −10 to −100 V was applied between the source electrode and drain electrode of the resultant organic TFT device, and then a gate voltage was changed in the range of −30 to −80 V to determine its voltage-current curve at a temperature of 25° C., followed by the evaluation of the device for its transistor characteristics. A field-effect mobility (μ) was calculated with the following equation (I) representing a drain current $I_d$.

$$I_d = (W/2L)\mu C_i (V_g - V_t)^2 \quad (I)$$

In the equation (I), L represents a gate length and W represents a gate width. In addition, $C_i$ represents the capacity of an insulating layer per unit area, $V_g$ represents the gate voltage, and $V_t$ represents a threshold voltage. In addition, an on/off ratio was calculated from a ratio between the maximum and minimum drain current values ($I_d$). Table 2 shows the characteristics of the resultant organic field-effect transistor.

Example 22

An organic TFT device was produced by performing the same operations as those of Example 21 except that: a solution (1 wt %) of the compound 2-23 in chloroform was used instead of the solution (1 wt %) of the compound 1-1 in chlorobenzene; and the spin coating was performed at room temperature under the conditions of 1,000 rpm and 30 seconds. Table 2 shows the characteristics of the resultant device.

Example 23

An organic TFT device was produced by performing the same operations as those of Example 21 except that: a solution (1 wt %) of the compound 2-24 in chloroform was used instead of the solution (1 wt %) of the compound 1-1 in chlorobenzene; and the spin coating was performed at room temperature under the conditions of 1,000 rpm and 30 seconds. Table 2 shows the characteristics of the resultant device.

Example 24

An organic field-effect transistor substrate was produced by the same method as that of Example 21. The substrate had a channel length L of 25 μm and a channel width W of 15.6 μm. Next, the compound 1-25 was deposited by a vacuum deposition method under the condition of a degree of vacuum of $5.0 \times 10^{-4}$ Pa onto the organic field-effect transistor substrate to form a thin film of the compound 1-25 having a thickness of 100 nm at 0.3 nm/sec. Thus, an organic TFT device having the structure illustrated in FIG. 2 was obtained. Table 2 shows the characteristics of the resultant device.

TABLE 2

| | Compound | Mobility (cm²/Vs) | On/off ratio |
|---|---|---|---|
| Example 21 | 1-1 | $2.8 \times 10^{-2}$ | $10^5$ |
| 22 | 2-23 | $8.6 \times 10^{-2}$ | $10^5$ |
| 23 | 2-24 | $8.8 \times 10^{-2}$ | $10^5$ |
| 24 | 1-25 | $9.3 \times 10^{-2}$ | $10^6$ |

Industrial Applicability

The chalcogen-containing aromatic compound to be used in the organic electroluminescence device of the present invention has a skeleton in which two aromatic heterocycles each having a chalcogen atom on a five-membered ring thereof are fused at [2,3-b] positions. The introduction of various substituents into the skeleton may enable the control of various energy values, i.e., an ionization potential, an electron affinity, and a triplet excitation energy. The presence of a skeleton having such specific fusion mode may improve stability against charge. In addition, the compound of the present invention has good planarity, and hence may have a high charge-transferring characteristic by virtue of a stacking effect between materials. Therefore, the organic electronic device of the present invention may be able to express high characteristics. The device may find applications in, for example, displays such as an organic EL panel and electronic paper, liquid crystal displays, organic field-effect transistors, organic thin-film solar cells, information tags, and large-area sensors such as an electronic artificial skin sheet and a sheet-type scanner, and hence its technical value is large.

The invention claimed is:

1. An organic semiconductor material, comprising an organic semiconductor material comprising a chalcogen-containing aromatic compound, which is represented by the general formula (1);

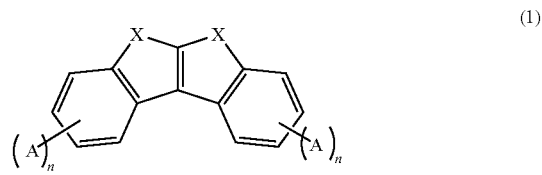

in the formula (1), X's each independently represent oxygen, sulfur, or selenium, A's each independently represent an alkyl group having 1 to 30 carbon atoms, a cycloalkyl group having 3 to 30 carbon atoms, to alkenyl group having 2 to 30 carbon atoms, an alkynyl group having 2 to 30 carbon atoms, an aromatic hydrocarbon group having 6 to 50 carbon atoms, an aromatic heterocyclic group having 3 to 50 carbon atoms and free of a fused heterocycle having 4 or more rings, or an amino group having 2 to 30 carbon atoms, and n's each independently represent an integer of 0 to 2, provided that a sum of two n's is an integer of 1 to 4.

2. An organic semiconductor thin film according to claim 1, wherein X's in the general formula (1) each independently represent oxygen or sulfur.

3. An organic electronic device, comprising an organic semiconductor material comprising a chalcogen-containing aromatic compound, which is represented by the general formula (1);

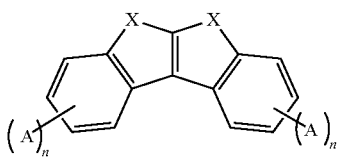

(1)

in the formula (1), X's each independently represent oxygen, sulfur, or selenium, A's each independently represent an alkyl group having 1 to 30 carbon atoms, a cycloalkyl group having 3 to 30 carbon atoms, to alkenyl group having 2 to 30 carbon atoms, an alkynyl group having 2 to 30 carbon atoms, an aromatic hydrocarbon group having 6 to 50 carbon atoms, an aromatic heterocyclic group having 3 to 50 carbon atoms and free of a fused heterocycle having 4 or more rings, or an amino group having 2 to 30 carbon atoms, and n's each independently represent an integer of 0 to 2, provided that a sum of two n's is an integer of 1 to 4.

4. An organic electronic device according to claim 3, wherein the organic electronic device comprises a device selected from a light-emitting device, a thin-film transistor, and a photovoltaic device.

5. An organic electronic device, according to claim 4, wherein the light-emitting device comprises an organic electroluminescence device.

6. An organic electronic device according to claim 3, wherein the organic electronic device comprises an organic electroluminescence device, the organic electroluminescence device has at least one organic layer, and at least one of the organic layer contains the organic semiconductor material.

7. An organic electronic device according to claim 6, wherein at least one of the organic layer of the organic electroluminescence device comprises a light-emitting layer containing a phosphorescent light-emitting dopant, and the light-emitting layer contains the organic semiconductor material.

8. An organic electronic device according to claim 3, wherein X's in the general formula (1) each independently represent oxygen or sulfur.

9. An organic electronic device according to claim 8, wherein two X's in the general formula (1) are identical to each other.

10. An organic electronic device according to claim 8, wherein the organic electronic device comprises a device selected from a light-emitting device, a thin-film transistor, and a photovoltaic device.

11. An organic electronic device according to claim 9, wherein the organic electronic device comprises a device selected from a light-emitting device, a thin-film transistor, and a photovoltaic device.

12. An organic electronic device according to claim 10, wherein the light-emitting device comprises an organic electroluminescence device.

13. An organic electronic device according to claim 11, wherein the light-emitting device comprises an organic electroluminescence device.

14. An organic electronic device according to claim 8, wherein the organic electronic device comprises an organic electroluminescence device, the organic electroluminescence device has at least one organic layer, and at least one of the organic layer contains the organic semiconductor material.

15. An organic electronic device according to claim 9, wherein the organic electronic device comprises an organic electroluminescence device, the organic electroluminescence device has at least one organic layer, and at least one of the organic layer contains the organic semiconductor material.

16. An organic electronic device according to claim 14, wherein at least one of the organic layer of the organic electroluminescence device comprises a light-emitting layer containing a phosphorescent light-emitting dopant, and the light-emitting layer contains the organic semiconductor material.

17. An organic electronic, device according to claim 15, wherein at least one of the organic layer of the organic electroluminescence device comprises a light-emitting layer containing a phosphorescent light-emitting dopant and the light-emitting layer contains the organic semiconductor material.

* * * * *